United States Patent
Wood et al.

(10) Patent No.: US 6,187,799 B1
(45) Date of Patent: *Feb. 13, 2001

(54) INHIBITION OF RAF KINASE ACTIVITY USING ARYL UREAS

(75) Inventors: Jill E Wood, Hamden, CT (US); Hanno Wild, Wuppertal (DE); Daniel H Rogers, San Diego; John Lyons, Moraga, both of CA (US); Michael Katz, Wallingford, CT (US); Yolanda Caringal, Branford, CT (US); Robert Dally, East Haven, CT (US); Wendy Lee, Hamden, CT (US); Roger A. Smith, Madison, CT (US); Cheri Blum, Alameda, CA (US)

(73) Assignees: Onyx Pharmaceuticals, Richmond, CA (US); Bayer Corporation, West Haven, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/083,399

(22) Filed: May 22, 1998

Related U.S. Application Data

(60) Provisional application No. 60/126,420, filed on May 23, 1997.

(51) Int. Cl.[7] .......................... A61K 31/38; C07D 409/00; C07D 333/42; C07D 307/02
(52) U.S. Cl. .......................... 514/363; 514/371; 514/397; 514/407; 514/414; 514/444; 514/445; 514/465; 514/585; 514/596; 548/140; 548/196; 548/315.1; 548/365.7; 548/465; 549/59; 549/69; 549/480
(58) Field of Search ..................... 548/557, 140, 548/196, 315.1, 365.7, 465; 549/69, 480, 59; 514/445, 585, 596, 363, 397, 444, 371, 414, 407

(56) References Cited

U.S. PATENT DOCUMENTS

| | | | |
|---|---|---|---|
| 3,424,760 | * | 1/1969 | Helsley et al. ................. 548/557 |
| 3,424,761 | * | 1/1969 | Helsley et al. ................. 548/557 |
| 3,424,762 | * | 1/1969 | Helsley et al. ................. 548/557 |
| 3,823,161 | | 7/1974 | Lesser ......................... 514/447 X |
| 3,828,001 | * | 8/1974 | Broad et al. ....................... 549/69 |
| 4,009,847 | * | 3/1977 | Aldrich et al. ................... 424/275 |
| 4,071,524 | * | 1/1978 | Banitt ............................. 548/557 |
| 4,111,683 | * | 9/1978 | Singer ......................... 549/480 X |
| 4,437,878 | * | 3/1984 | Acker et al. ................. 549/69 X |
| 4,643,849 | * | 2/1987 | Hirai et al. ...................... 540/955 |
| 4,740,520 | | 4/1988 | Hallenbach et al. ............ 514/447 |
| 4,808,588 | | 2/1989 | King ............................. 514/212 |
| 5,130,331 | | 7/1992 | Pascual ......................... 514/447 |
| 5,597,719 | | 1/1997 | Freed et al. ..................... 435/194 |
| 5,773,459 | * | 6/1998 | Tang et al. ..................... 514/445 |

FOREIGN PATENT DOCUMENTS

| | | | |
|---|---|---|---|
| 2146707 | | 10/1995 | (CA) . |
| 3305866 | * | 8/1984 | (DE) ............................... 549/69 |
| 54-32468 | * | 3/1979 | (JP) ............................... 548/557 |
| 93/24458 | | 12/1993 | (WO) . |
| 97/49400 | | 12/1994 | (WO) . |
| 95/02591 | | 1/1995 | (WO) . |
| 95/07922 | | 3/1995 | (WO) . |
| 95/13067 | | 5/1995 | (WO) . |
| 95//131451 | | 11/1995 | (WO) . |
| 96/40673 | | 12/1996 | (WO) . |
| 97/49399 | | 12/1997 | (WO) . |
| 99/00357 | | 1/1999 | (WO) . |

OTHER PUBLICATIONS

Avruch et al., "Raf meets Ras: completing the framework of a signal transduction pathway", TIBS 19; Jul. 1994; pp. 279–2823.

Daum et al., "The ins and outs of Raf kinases", TIBS 19–Nov. 1994; pp. 474–480.

Kolch et al., "Raf–1 protein kinase is required for growth of induced NIH/3T3 cells", Letters to Nature, vol. 349, 31 Jan. 91, pp. 426–428, 1991.

Fridman et al., "The Minimal Fragments of c–Raf–1 and NF1 That Can Suppress v–Ha–Ras–Induced Malignant Phenotype", J. of Biol. Chem., vol. 269, No. 48, pp. 30105–30108, 1994.

Bolton et al., "Ras Oncogene Directed Approaches in Cancer Chemotherapy", Ann. Reports in Medicinal Chemistry–29, pp. 165–174.

Johannes L. Bos, "ras Oncogenes in Human Cancer: A Review", Cancer Research, vol. 49, 4682–4689, Sep.1, 1989.

Magnuson et al., "The Raf–1 serine/threonine protein kinase", Seminars in Cancer Biology, vol. 5, 1994, pp. 247–253.

Tarzia, G. et al. Whythesis and antiinflammatory properties of some pyrrolo(1H, 3H)[3,4–d] pyrimidin–2–onesandpyrrolo(1H,3H)[3,4–d] pyurimidin–2–ones and pyrrolo(1H,3H)–pyrimidin–2–ones. Chemical Abstracts. 27 Aug. 1979, No. 74558p; p. 594.

Database CA on STN, EP 676395 A1 (Hoechst A.G., Germany), No. 124:86809, KLEEMANN et al., "Preparation of (pyrrolyl–and thienylcarbonyl)guanidines as sodium–hydrogen exchange inhibitors, antiarrhymic agents, and cell proliferation inhibitors." Abstract, Hanno Wild, 17 Jul. 1996.

* cited by examiner

Primary Examiner—Floyd D. Higel
(74) Attorney, Agent, or Firm—Millen, White, Zelano, & Branigan, P.C.

(57) ABSTRACT

Methods of treating tumors mediated by raf kinase, with substituted urea compounds, and such compounds per se.

18 Claims, No Drawings

INHIBITION OF RAF KINASE ACTIVITY USING ARYL UREAS

This application claims priorty to provisional application Ser. No. 60/126,420, filed May 23, 1997.

BACKGROUND OF THE INVENTION

The p21$^{ras}$ oncogene is a major contributor to the development and progression of human solid cancers and is mutated in 30% of all human cancers; Bolton et al., Annual Reports in Medicinal Chemistry, 29, 165–174 (1994); Bos, Cancer Res., 49, 4682 (1989).

In its normal, unmutated form, the ras protein is a key element of the signal transduction cascade directed by growth factor receptors in almost all tissues. See J. Avruch et al., TIBS (19), 279–283 (1994). Biochemically, ras is a guanine nucleotide binding protein, and cycling between a GTP-bound activated and a GDP-bound resting form is strictly controlled by ras' endogenous GTPase activity and other regulatory proteins. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants, Magnuson et al., Cancer Biology, 5, 247–253 (1994). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype. See Daum et al., TIBS 196, 474–480 (1994), and Fridman et al., J. Biol. Chem., 269, 30105–30108 (1994). Kolch et al., Nature, 349, 426–428 (1991), have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types; Monia et al., Nature Medicine, 2(6):668–675 (1996).

SUMMARY OF THE INVENTION

The present invention is directed to compounds and methods for the treatment of cancerous cell growth mediated by raf kinase. The compounds of the formulae

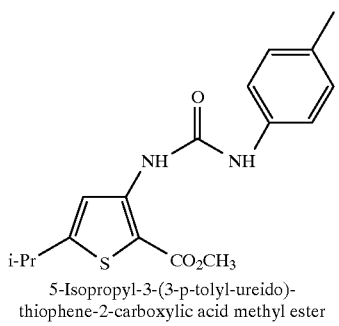

5-Isopropyl-3-(3-p-tolyl-ureido)-
thiophene-2-carboxylic acid methyl ester

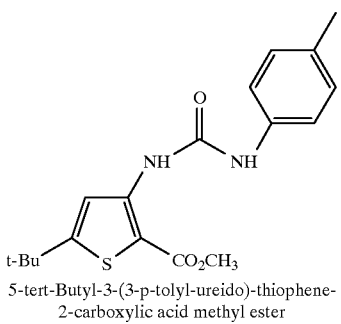

5-tert-Butyl-3-(3-p-tolyl-ureido)-thiophene-
2-carboxylic acid methyl ester

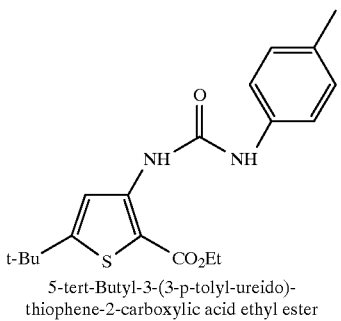

5-tert-Butyl-3-(3-p-tolyl-ureido)-
thiophene-2-carboxylic acid ethyl ester

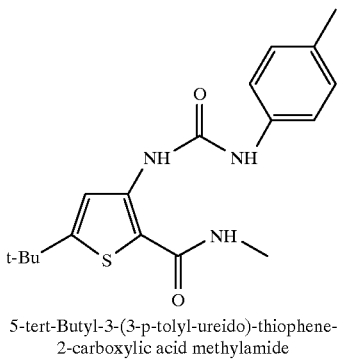

5-tert-Butyl-3-(3-p-tolyl-ureido)-thiophene-
2-carboxylic acid methylamide

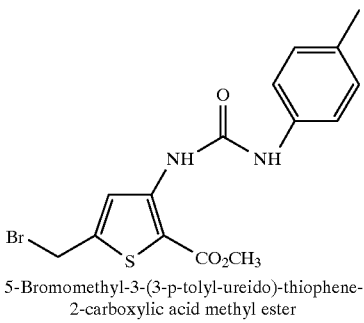

5-Bromomethyl-3-(3-p-tolyl-ureido)-thiophene-
2-carboxylic acid methyl ester

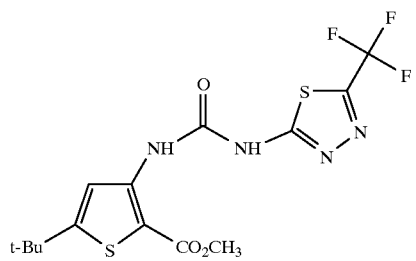

5-tert-Butyl-3-[3-(5-trifluoromethyl-[1,3,4]-thiadiazol-2-yl)-ureido]-thiophene-2-carboxylic acid methyl ester

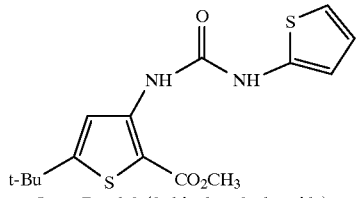

5-tert-Butyl-3-(3-thiophen-2-yl-ureido)-thiophene-2-carboxylic acid methyl ester

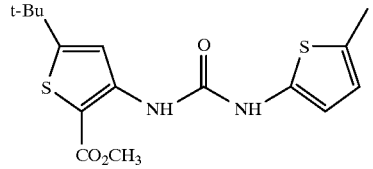

5-tert-Butyl-3-[3-(5-methyl-thiophen-2-yl)ureido]-thiophene-2-carboxylic acid methyl ester

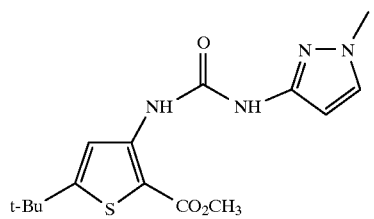

5-tert-Butyl-3-[3-(1-methyl-1H-pyrazol-3-yl)-ureido]-thiophene-2-carboxylic acid methyl ester

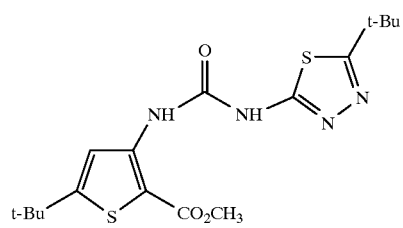

5-tert-Butyl-3-[3-(5-tert-butyl-[1,3,4]thiadiazol-2-yl)-ureido]-thiophene-2-carboxylic acid methyl ester

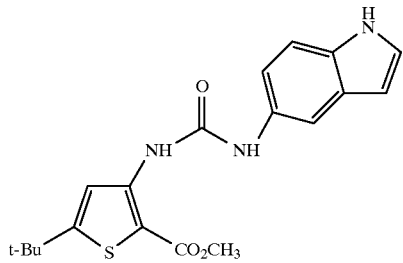

5-tert-Butyl-3-[3-(1H-indol-5-yl)-ureido]-thiophene-2-carboxylic acid methyl ester

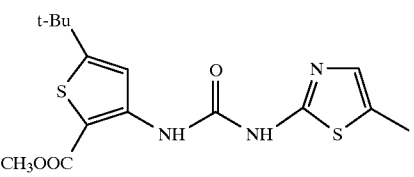

5-tert-Butyl-3-[3-(5-methyl-thiazol-2-yl)ureido]-thiophene-2-carboxylic acid methyl ester

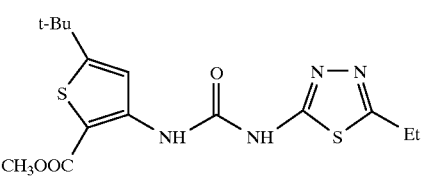

5-tert-Butyl-3-[3-(5-ethyl-[1,3,4]thiadiazol-2-yl)-ureido]-thiophene-2-carboxylic acid methyl ester

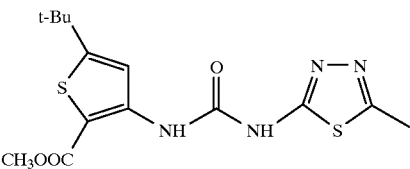

5-tert-Butyl-3-[3-(5-methyl-[1,3,4]thiadiazol-2-yl)-ureido]-thiophene-2-carboxylic acid methyl ester

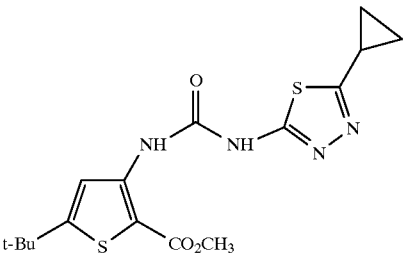

5-tert-Butyl-3-[3-(5-cyclopropyl-[1,3,4]thiadiazol-2-yl)ureido]-thiophene-2-carboxylic acid methyl ester

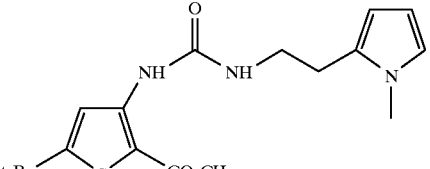

5-tert-Butyl-3-{3-[2-(1-methyl-1H-pyrrol-2-yl)-ethyl]-ureido}-thiophene-2-carboxylic acid methyl ester

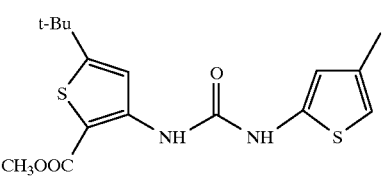

5-tert-Butyl-3-[3-(4-methyl-thiophen-2-yl)ureido]-thiophene-2-carboxylic acid methyl ester -continued

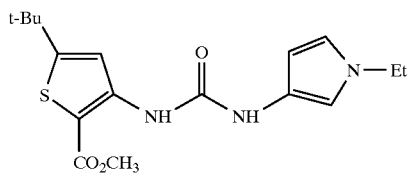
5-tert-Butyl-3-[3-(1-ethyl-1H-pyrrol-3-yl)-ureido]-
thiophene-2-carboxylic acid methyl ester

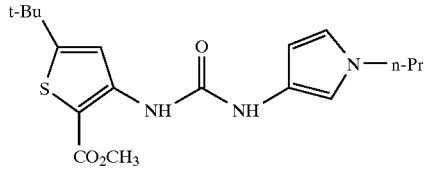
5-tert-Butyl-3-[3-(1-propyl-1H-pyrrol-3-yl)-ureido]-
thiophene-2-carboxylic acid methyl ester

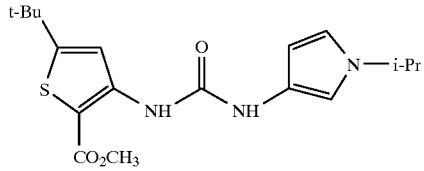
5-tert-Butyl-3-[3-(1-isopropyl-1H-pyrrol-3-yl)-
ureido]-thiophene-2-carboxylic acid methyl ester

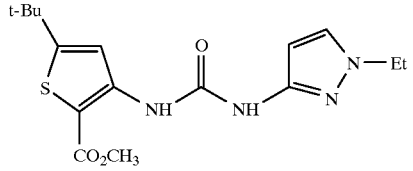
5-tert-Butyl-3-[3-(1-ethyl-1H-pyrazol-3-yl)-
ureido]-thiophene-2-carboxylic acid methyl ester

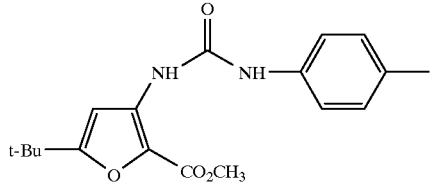
5-tert-Butyl-3-(3-p-tolyl-ureido)-furan-
2-carboxylic acid methyl ester

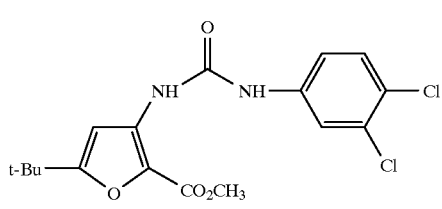
5-tert-Butyl-3-[3-(3,4-dichloro-phenyl)-ureido]-
furan-2-carboxylic acid methyl ester

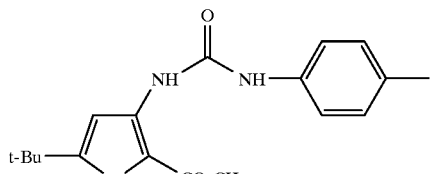
5-tert-Butyl-3-(3-p-tolyl-ureido)-1H-pyrrole-
2-carboxylic acid methyl ester -continued

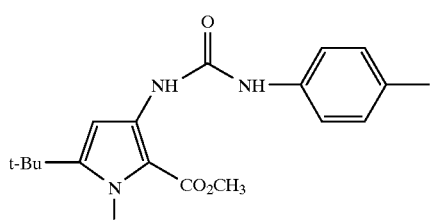
5-tert-Butyl-1-methyl-3-(3-p-tolyl-ureido)-
1H-pyrrole-2-carboxylic acid methyl ester

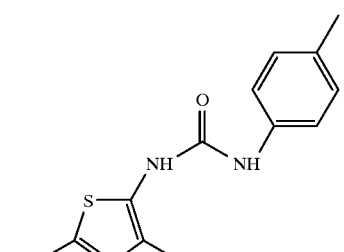
5-tert-Butyl-2-(3-p-tolyl-ureido)-thiophene-
3-carboxylic acid methyl ester

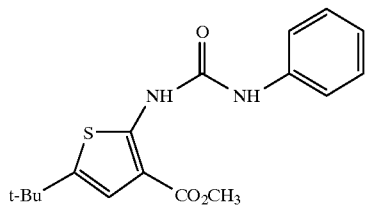
5-tert-Butyl-2-(3-phenyl-ureido)-thiophene-
3-carboxylic acid methyl ester

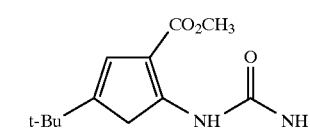

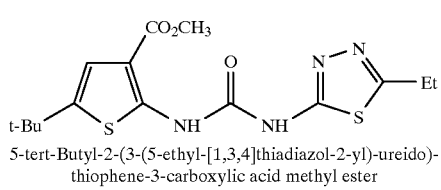
5-tert-Butyl-2-(3-(5-ethyl-[1,3,4]thiadiazol-2-yl)-ureido)-
thiophene-3-carboxylic acid methyl ester

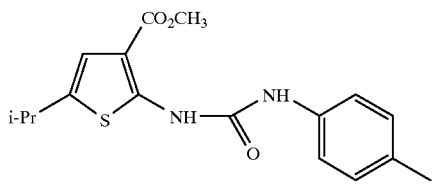
5-Isopropyl-2-(3-p-tolyl-ureido)-thiophene-
3-carboxylic acid methyl ester or

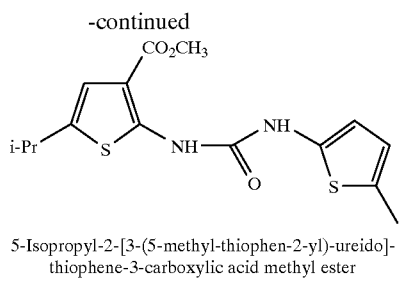
5-Isopropyl-2-[3-(5-methyl-thiophen-2-yl)-ureido]-thiophene-3-carboxylic acid methyl ester
(where Et is ethyl, Pr is propyl, and Bu is butyl).
Preferred compounds include, e.g.,
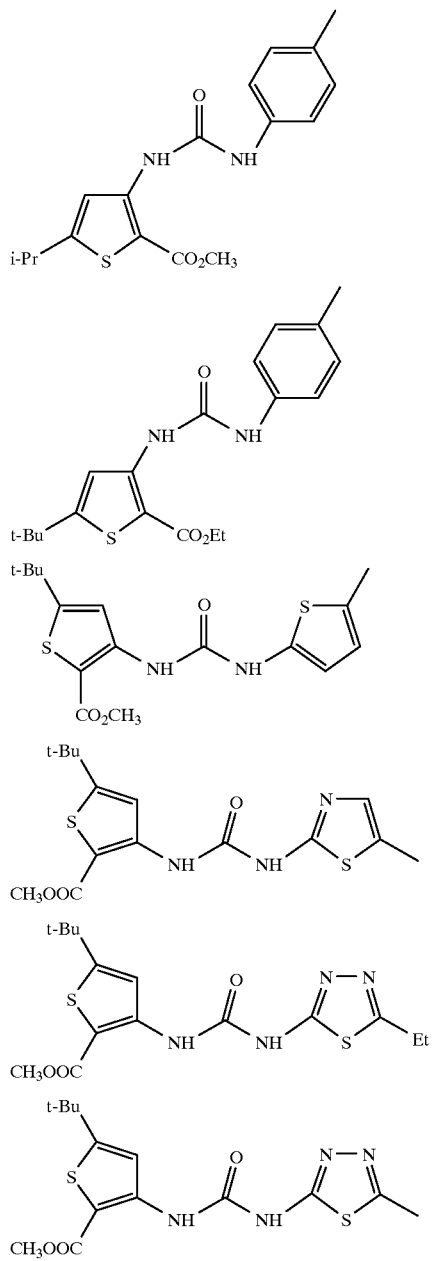
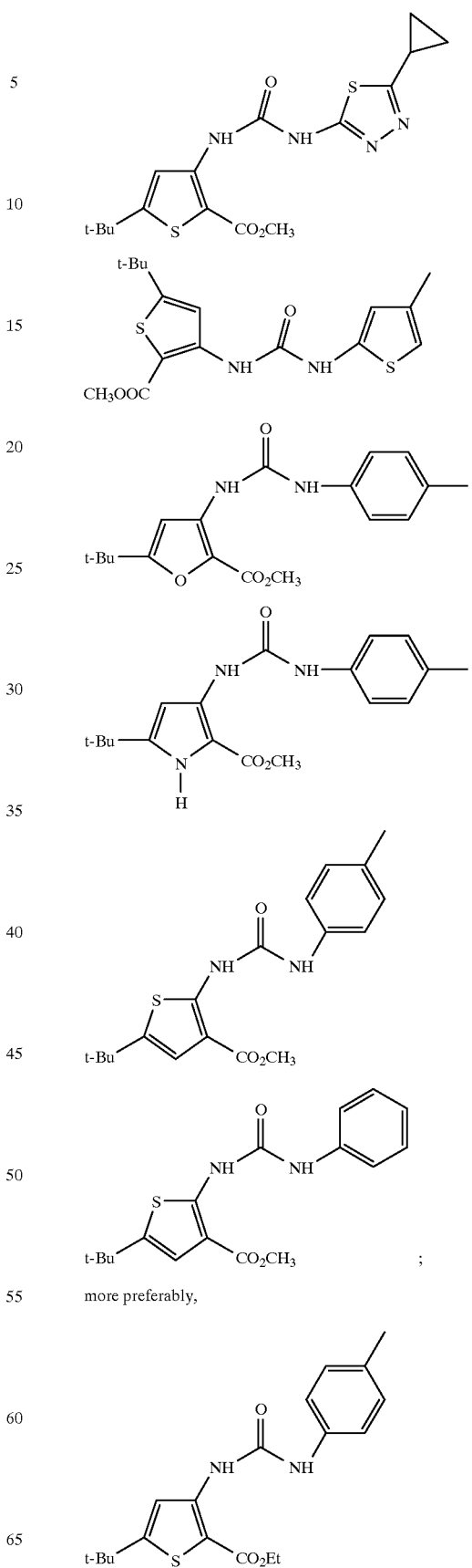
more preferably,

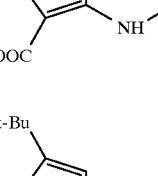

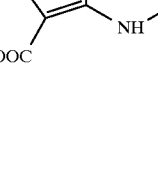

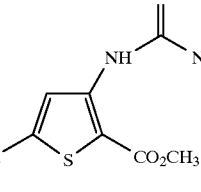

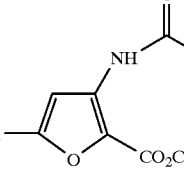

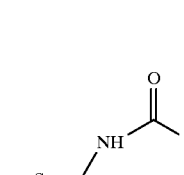

The compounds may be administered orally, topically, parenterally, by inhalation or spray or rectally in dosage unit formulations. The term parenteral as used herein includes subcutaneous injections, intravenous, intramuscular, intrasternal injection or infusion techniques. One or more compounds may be present in association with one or more non-toxic pharmaceutically acceptable carriers and if desired other active ingredients. The preferred method of administration is parenteral.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example, lecithin, or condensation products or an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

It will be appreciated by those skilled in the art that the particular method of administration will depend on a variety of factors, all of which are considered routinely when administering therapeutics.

The compounds of the invention are typically employed at a dosage of 0.01 to 200 mg/kg per day, preferably 200 mg/kg ip.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

The compounds of the invention are inhibitors of the enzyme raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine, solid cancers, since the progression of these cancers is dependent upon the ras protein signal transduction cascade and therefore susceptible to treatment by interruption of the cascade, i.e., by inhibiting raf kinase.

The activity of a given compound to inhibit raf kinase can be routinely assayed, e.g., according to procedures disclosed herein.

In such an in vitro kinase assay, raf is incubated either alone or with MEK in 20 mM Tris-HCl, pH 8.2 containing 2 mM 2-mercaptoethanol and 100 mM NaCl. Twenty microliters of this protein solution are mixed with 5 μl of water or compounds diluted with distilled water from 10 mM stock solutions of compounds dissolved in DMSO. The kinase reaction is initiated by adding 25 μl [γ-$^{33}$P]ATP (1000–3000 dpm/pmol) in 80 mM Tris-HCl, pH 7.5, 120 mM NaCl, 1.6 mM DTT, 16 mM $MgCl_2$. The reaction mixtures are incubated at 32° C., usually for 22 minutes and incorporation of $^{33}$P into protein is assayed by harvesting the reaction onto phosphocellulose mats, washing away free counts with 1% phosphoric acid and quantitating phosphorylation by liquid scintillation counting. For high throughput screening, 10 μM ATP and 0.4 μM MEK are used. In some experiments, the kinase reaction is stopped by adding an equal amount of Laemmli sample buffer. Samples are boiled 3 minutes and the proteins resolved by electrophoresis on 7.5% Laemmli gels. Gels are fixed, dried and exposed to an imaging plate (Fuji). Phosphorylation is analyzed using a Fujix Bio-Imaging Analyzer System. Protein kinase C (0.05 mU; Boehringer Mannheim) phosphorylation of histone H1 is assayed according to manufacturer's instructions.

For in vitro growth assay, untransformed NIH3T3 fibroblast or transformed fibroblasts stably expressing their v-H-ras, v-Raf or v-fos are obtained (Onyx). The fibroblast lines are maintained in Dulbecco's Modified Eagle's Medium with high glucose containing 10% fetal bovine serum and 200 mM glutamine. Human colon carcinoma cell lines, DLD-1, Colo 205 and HCT116 are obtained from ATCC (Rockville, Md.) and maintained in RPMI with 10% fetal bovine serum and 200 mM glutamine. Cell culture media and additives are obtained from Gibco/BRL (Gaithersburg, Md.) except for fetal bovine serum (JRH Biosciences, Lenexa, Kans.). In some experiments, $3 \times 10^3$ cells are seeded into 96-well plates and allowed to grow overnight at 37° C. in a 5% $CO_2$ incubator. Proliferation is determined by allowing the cells to incorporate $^3$H-thymidine during the last 18 hours of culture, harvesting cells onto glass fiber mats and measuring $^3$H-thymidine incorporation by liquid scintillation counting.

These assays establish that the compounds of formula I are active to inhibit raf kinase activity and to inhibit oncogenic cell growth.

An in vivo assay of the inhibitory effect of the compounds on tumors (e.g., solid cancers) mediated by raf kinase can be performed as follows:

CDI nu/nu mice (6–8 weeks old) are injected subcutaneously into the flank at $1 \times 10^6$ cells with human colon adenocarcinoma cell line . The mice are dosed ip at 50, 100, and 200 mg/kg beginning on day 10, when tumor size is between 50–100 mg. Animals are dosed for 10 consecutive days once a day; tumor size was monitored with calipers twice a week to day 35.

The inhibitory effect of the compounds on raf kinase and therefore on tumors (e.g., solid cancers) mediated by raf kinase can further be demonstrated in vivo according to the technique of Monia et al., Nature Medicine, 2(6):668–675 (1996).

Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

The compounds of formulae 1-31 are producible from known compounds (or from starting materials which, in turn, are producible from known compounds), e.g., through the general preparative methods shown below:

Method A

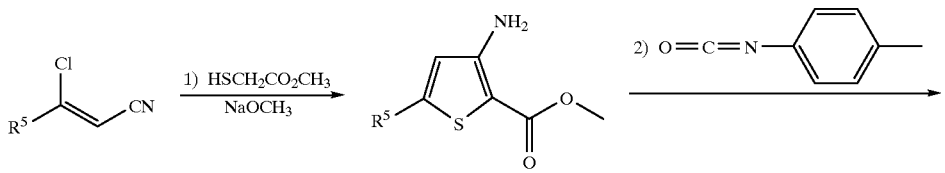

-continued
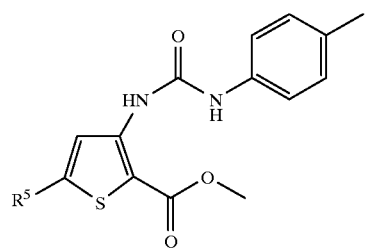
Method B
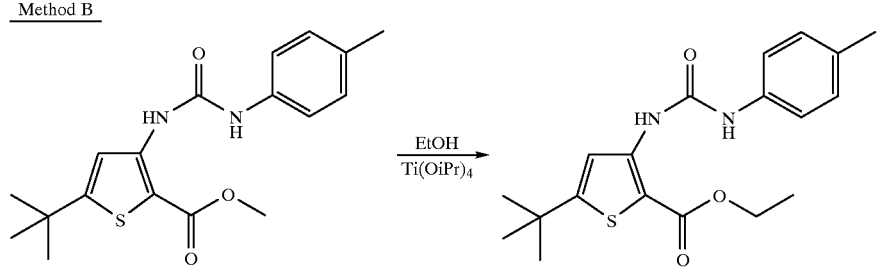
Method C
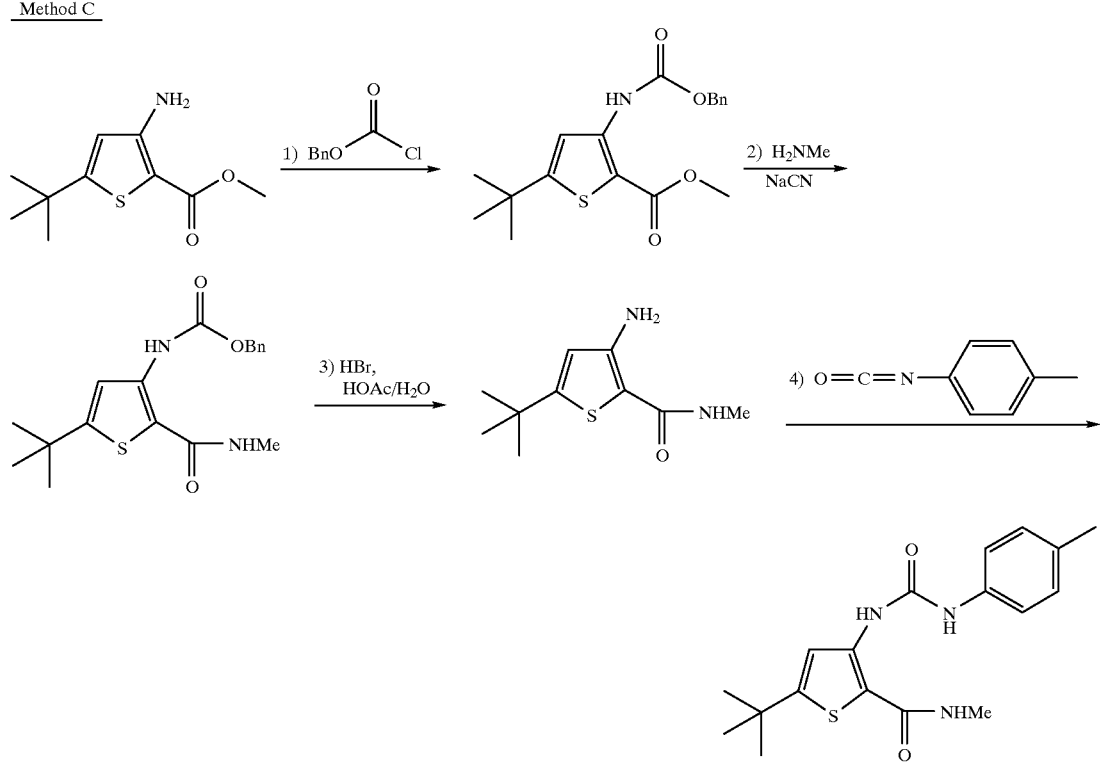
Method D
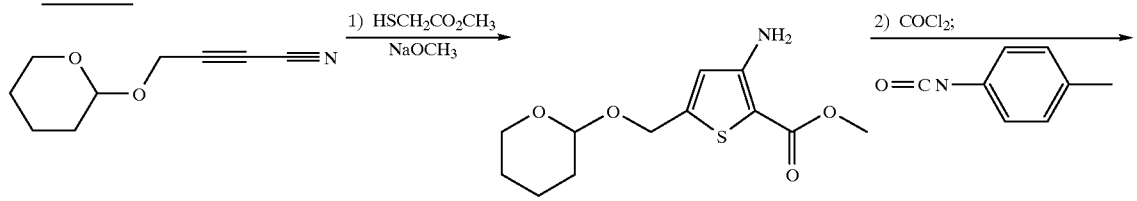

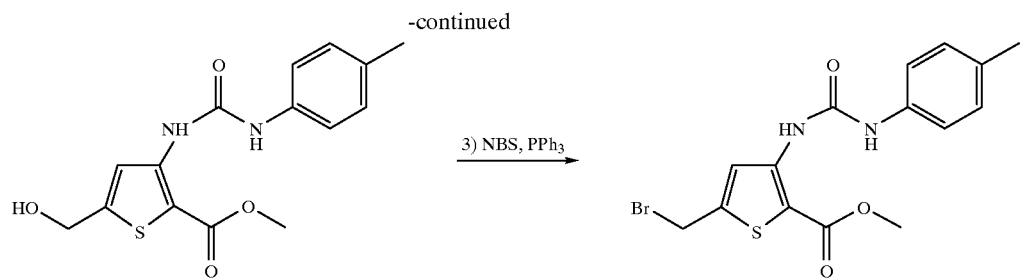
Method E
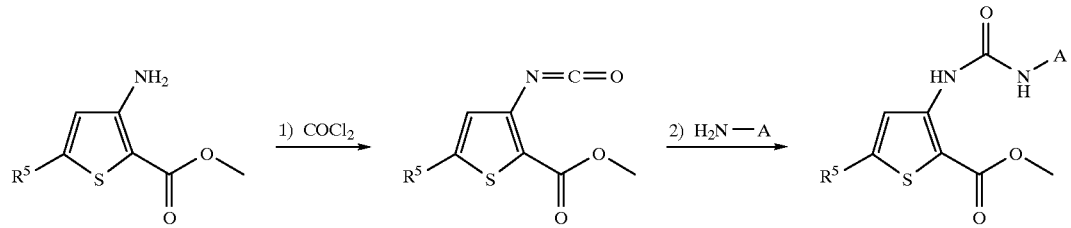
Method F
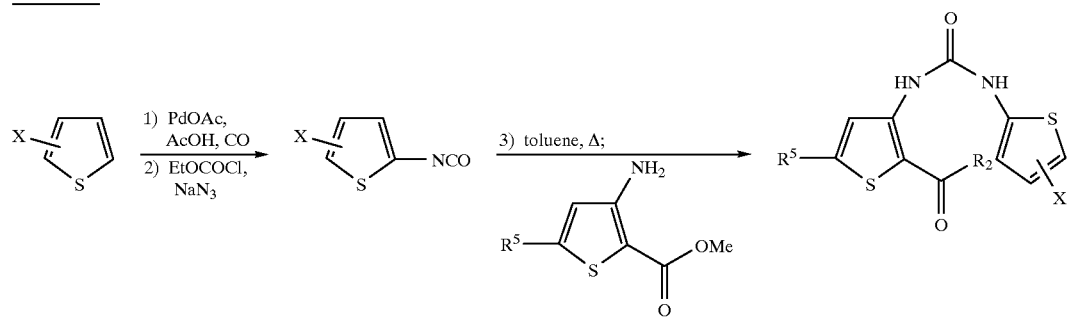
Method G
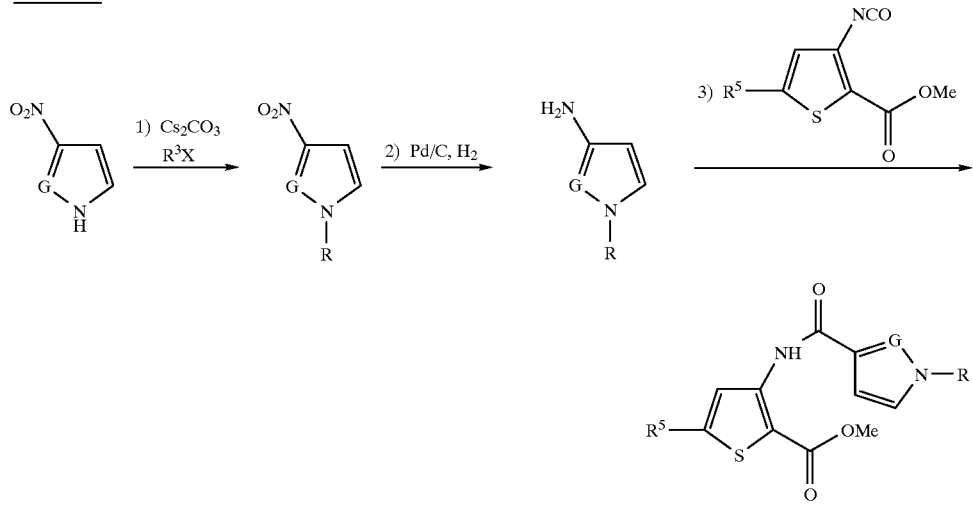
G = CH, N
Method H
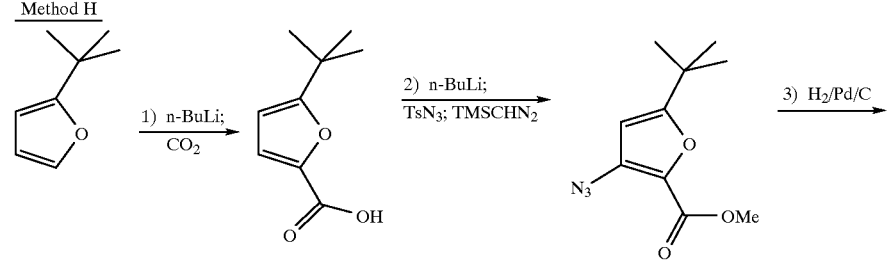

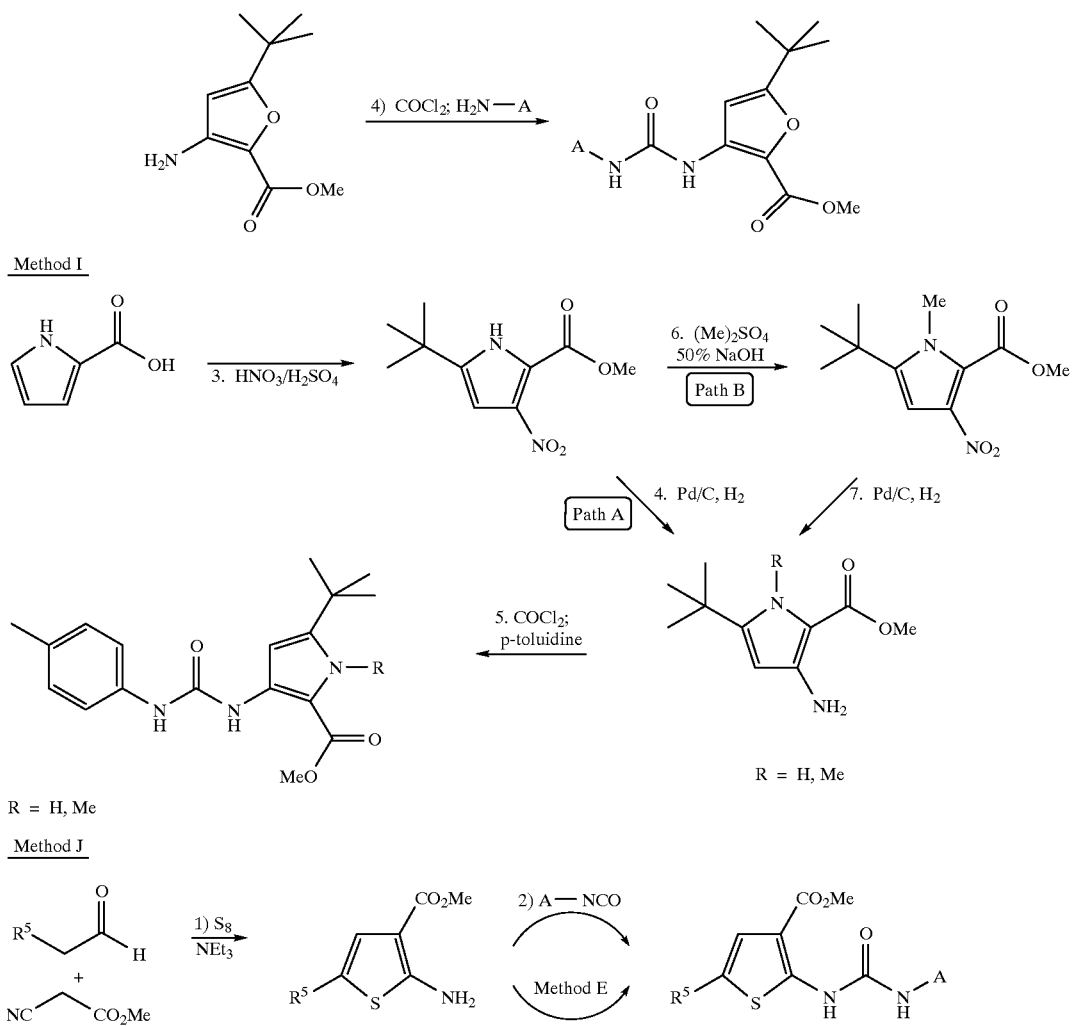

Abbreviations used:
Ac, acyl; Ar, aryl; Boc, t-butoxycarbonyl; Bn, benzyl; Cbz, carbobenzyloxy; DCC, dicyclohexylcarbodiimide; DMAP, 4-dimethylaminopyridine; DMF, N,N-dimethylformamide; Et, ethyl; EtOAc, ethyl acetate; LRMS, low resolution mass spectrometry; Me, methyl; NMM, N-methyl morpholine; Ph, phenyl; Pr, propyl; pyr., pyridine; TLC, thin layer chromatography; TFA, trifluoroacetic acid; TMS, trimethylsilyl; Ts, p-toluenesulfonyl.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and, unless otherwise indicated, all parts and percentages are by volume.

The entire disclosure of all applications, patents and publications, cited above and below, are hereby incorporated by reference.

EXAMPLES

Experimental:

Flash chromatography was run using Silica Gel 60 (230–400 mesh size) from EM Science. Mass spectral data were obtained on a Krato-MS 80RFA spectrometer using the fast atom bombardment technique (FAB) unless otherwise noted. Melting points were taken on a Thomas-Hoover Uni-Melt apparatus and are not corrected.

TABLE 1

3-Urea Thiophenes

| Example # | $R^5$ | $R^2$ | Method | mp °C. or LRMS |
|---|---|---|---|---|
| 1 | i-Pr | COOMe | A | 93–95 |
| 2 | t-Bu | COOMe | A | 124–126 |
| 3 | t-Bu | COOEt | B | $(M + H)^+ = 361$ |
| 4 | t-Bu | CONHMe | C | 230–231 |
| 5 | $CH_2Br$ | COOMe | D | 157–158 |

TABLE 2

Heteroaryl substitution for A

| Example # | A | Method | mp °C. or LRMS |
|---|---|---|---|
| 6 | 1,3,4-thiadiazol-2-yl, 5-CF₃ | E | (M + H)⁺ = 409 |
| 7 | thien-2-yl | F | (M + H)⁺ = 339 |
| 8 | 5-methylthien-2-yl | F | (M + H)⁺ = 353 |
| 9 | 1-methylpyrazol-3-yl | E | 186–188 |
| 10 | 1,3,4-thiadiazol-2-yl, 5-t-butyl | E | (M + H)⁺ = 397 |
| 11 | 1H-indol-5-yl | E | (M + H)⁺ = 372 |
| 12 | 5-methylthiazol-2-yl | E | 215–216 |
| 13 | 1,3,4-thiadiazol-2-yl, 5-ethyl | E | 168–170 |

TABLE 2-continued

Heteroaryl substitution for A

| Example # | A | Method | mp °C. or LRMS |
|---|---|---|---|
| 14 | 1,3,4-thiadiazol-2-yl, 5-methyl | E | 229–231 |
| 15 | 1,3,4-thiadiazol-2-yl, 5-cyclopropyl | E | (M + H)⁺ = 381 |
| 16 | 1-methylpyrrol-2-yl (propyl linker) | E | (M + H)⁺ = 364 |
| 17 | 4-methylthien-2-yl | F | (M + H)⁺ = 353 |
| 18 | 1-ethylpyrrol-3-yl | G | (M + H)⁺ = 350 |
| 19 | 1-propylpyrrol-3-yl | G | (M + H)⁺ = 364 |
| 20 | 1-isopropylpyrrol-3-yl | G | (M + H)⁺ = 364 |
| 21 | 1-ethylpyrazol-3-yl | G | (M + H)⁺ = 351 |

TABLE 3

Furyl or pyrrole substitution for B.

| Example # | B | X | Method | LRMS |
|---|---|---|---|---|
| 22 | 3-tBu-5-(CO2Me)-furan-2-yl | 4-Me | H | (M + H)+ = 331 |
| 23 | 3-tBu-5-(CO2Me)-furan-2-yl | 3,4-diCl | H | M+ = 384 EI |
| 24 | 3-tBu-5-(CO2Me)-pyrrol-2-yl (NH) | 4-Me | I | (M + H)+ = 330 |
| 25 | 3-tBu-5-(CO2Me)-N-Me-pyrrol-2-yl | 4-Me | I | M+ = 343 |

TABLE 4

2-Urea Thiophenes

| Example # | R⁵ | A | Method | mp °C |
|---|---|---|---|---|
| 26 | t-Bu | 4-Me—Ph | J | 109–111 |
| 27 | t-Bu | Ph | J | 80–82 |

TABLE 4-continued

2-Urea Thiophenes

| Example # | R⁵ | A | Method | mp °C |
|---|---|---|---|---|
| 28 | t-Bu | 5-ethyl-1,3,4-thiadiazol-2-yl | J | 206–208 |
| 29 | iPr | 4-Me—Ph | J | 49–51 |
| 30 | iPr | 5-methyl-thiophen-2-yl | J | 70–73 |

The following compounds have been synthesized according to the general methods listed above:

Method A

Synthesis of 5-Isopropyl-3-(3-p-tolyl-ureido)-thiophene-2-carboxylic acid methyl ester. (Example 1)

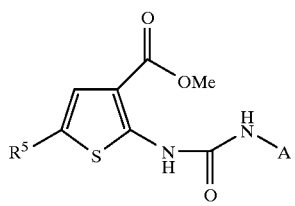

Step 1

To a suspension of sodium methoxide (14 g) in methanol (1 L) was added methyl thioglycolate (22.3 mL). The solution was stirred 5 min, then 3-chloro-4-methyl-2-pentenenitrile (32.4 g) [Hackler, R. E. et al. J. Heterocyclic Chem. 1989, 26, 1575; Hartmann, H.; Liebscher, J. Synthesis 1984, 275; Gupton, J. T. et al. Synthetic Comm. 1982, 12, 34] in methanol (200 mL) was added and the solution was heated to reflux for 90 min. After cooling to 20° C., the solvent was removed in vacuo. The residue was dissolved in ethyl acetate and was washed with 1N HCl, dried over $MgSO_4$ and the solvent was removed in vacuo. The residue was purified by flash chromatography using hexane/ethyl acetate mixtures to yield 8.0 g (16%) of the desired amino thiophene.

Step 2

A solution of 3-amino-5-isopropyl-2-methyl ester-thiophene (233 mg) in toluene (10 mL) was heated to reflux. A solution of p-methylphenyl isocyanate (150 uL) in toluene (5 mL) was added via a syringe pump over 1 h. The reaction was heated to reflux for 1 h, cooled to 20° C. and the solvent removed in vacuo. The residue was purified by flash chromatography using hexane/dichloromethane mixtures to yield 265 mg (68%) of Example 1 as a foam. $^1$H NMR (CDCl$_3$) d 1.28 (s, 6H), 2.30 (s, 3H), 3.06 (m, 1H), 3.75 (s, 3H), 7.11 (d, 2H), 7.30 (d, 2H), 7.72 (s, 1H), 7.83 (s, 1H), 9.67 (s, 1H).

5-tert-Butyl-3-(3-p-tolyl-ureido)-thiophene-2-carboxylic acid methyl ester (example 2) was synthesized according to this procedure using 3-chloro4,4-dimethyl-2-pentenenitrile in place of the 3-chloro4-methyl-2-pentenenitrile.

Method B

Synthesis of 5-tert-Butyl-3-(3-p-tolyl-ureido)-thiophene-2-carboxylic acid ethyl ester. (Example 3)

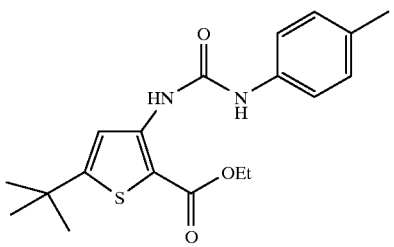

A solution of titanium isopropoxide (1 mL), methyl 3-(4-methyl phenyl urea)-5-tert-butyl thiophene-2-carboxylate (500 mg, 1.44 mmol), and ethanol (10 mL) was heated to for 24 h. Solvent was removed in vacuo and the resultant oil was dissolved in methylene chloride and purified by flash chromatography (ethyl acetate/hexane). Concentration in vacuo afforded 119 mg (23%) of Example 3. $^1$H NMR (CDCl$_3$) d 9.71 (s, 1H); 7.87 (s, 1H); 7.29 (d, J=8.5 Hz, 2H); 7.15 (d, J=8.1 Hz, 2H); 4.28 (q, J=7.4 Hz, 2H); 2.33 (s, 3H); 1.29 (m, 12H).

Method C

Synthesis of 5-tert-Butyl-3-(3-p-tolyl-ureido)-thiophene-2-carboxylic acid methylamide. (Example 4)

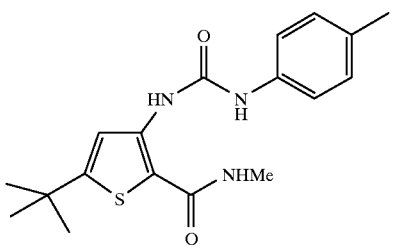

Step 1

A solution of methyl-3-amino-5-t-butylthiophene-2-carboxylate (20.0 g, 93.9 mmol), benzyl chloroformate (80.4 mL, 563 mmol), sodium carbonate (1.10 g, 9.93 mmol), toluene (400 mL) and water (50 mL) was kept at reflux 18 h. Solvent was removed in vacuo and resulting oil dissolved in ethyl acetate, washed with water, brine, dried over magnesium sulfate and concentrated in vacuo affording the corresponding benzyl carbamate ester in quantitative crude yield.

Step 2

The carbamate ester (13.6 g, 39.2 mmol) was dissolved in saturated methyl amine/methanol (200 mL) in a screw top vessel. Sodium cyanide (0.98 g, 20 mmol) was suspended in the solution. The vessel was sealed and heated to 50° C. for 8 h. The solution was poured into water (500 mL) and extracted with ethyl acetate. The ethyl acetate layer was then washed with water, brine, dried over sodium sulfate, and concentrated in vacuo. The crude material was purified by flash chromatography with ethyl acetate/hexane affording 2.76 g (20%) of the N-methyl amide carbamate.

Step 3

The carbamate (2.76 g, 8 mmol) was then dissolved in 100 mL of 1:1 48% hydrobromic acid/acetic acid and heated to 30° C. for 24 h. The acidic solution was cooled and basidified to pH 4 with saturated sodium bicarbonate. Methyl amine (4 mL, 2 M) in tetrahydrofuran was added before extraction with methylene chloride. Solvent was removed in vacuo affording 922.5 mg (54%) of the N-methyl amide amine.

Step 4

A solution of the amine (600 mg, 2.83 mmol), p-tolyl isocyanate (356.4 uL, 2.83 mmol) and 2 mL toluene was heated to reflux for 18 h. Solvent was removed in vacuo and the resulting solid was purified by flash chromatography with ethyl acetate/methylene chloride affording 417 mg (44%) of Example 4. $^1$H NMR (CDCl$_3$) d 10.53 (s, 1h); 7.90 (s, 1h); 7.29 (d, 2H, J=8.5 Hz); 7.11 (d, 2H, J=8.5 Hz); 5.59 (bs, 1h); 2.91 (d, 3H, J=4.9 Hz); 2.31 (s,3H);1.38 (s,9H); mp 202–204° C.

Method D

Synthesis of 5-Bromomethyl-3-(3-p-tolyl-ureido)-thiophene-2-carboxylic acid methyl ester. (Example 5)

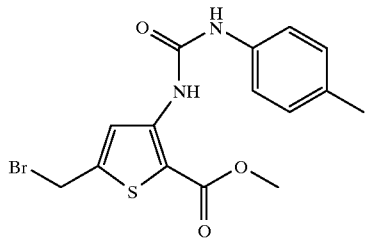

Step 1

To a dry three-necked flask containing anhydrous methanol (10 mL) kept cold with an ice-water bath was added sodium spheres (116 mg, 5.06 mmol). After the sodium spheres were completely dissolved, methyl thioglycolate (537 mg, 5.06 mmol) was added. After ca. 5 min, a solution of crude 4-(2-tetrahydropyranoxy)-2-butyl-nitrile (0.76 g, 4.60 mmol) [Murray, R.; Zweifel, G., Synthesis, 1980, 150] in methanol (10 mL) was added to the mixture. The mixture was allowed to warm up to rt and maintained at this temperature for 2 h. The mixture was concentrated and the concentrate was partitioned between EtOAc (100 mL) and H$_2$O (50 mL). The organic layer was washed with brine (2×50 mL), dried (MgSO$_4$), and concentrated in vacuo. The crude product was purified by Chromatotron (4 mm plate, hexane-EtOAc, 9:1) to afford the aminothiophene (593 mg, 48%) as an orange oil. $^1$H NMR (CDCl$_3$) d 6.57 (s, 1H); 5.00 (br s, 2H); 4.79–4.72(m, 1H); 4.62 (s, 2H); 3.90–3.80 (m, 1H); 3.82 (s, 3H); 3.58–3.53 (m, 1H); 1.90–1.52 (m, 6H); GC-MS 271 [M]$^+$.

Step 2

The amine in Step 1 was converted to 5-hydroxymethyl-3-(3-p-tolyl-ureido)-thiophene-2-carboxylic acid methyl ester following Method E using toluidine in place of 2-amino-5-trifluoromethyl-1,3,4-thiadiazole. $^1$H NMR (DMSO-d$_6$) d 9.86 (s, 1H); 9.48 (s, 1H); 7.83 (s, 1H); 7.34 (d, J=8.1 Hz, 2H); 7.07 (d, J=8.5 Hz, 2H); 5.71 (t, J=5.0 Hz, 1H); 4.61 (d, J=4.4 Hz, 2H); 3.79 (s, 3H); 2.21 (s, 3H); MS (FAB-LSIMS) 321.2 [M+H]$^+$; mp 166–168° C.

Step 3

To a solution of 5-hydroxymethyl-3-(3-p-tolyl-ureido)-thiophene-2-carboxylic acid methyl ester (25 mg, 0.078 mmol) in anhydrous DMF (2 mL) was added N-bromosuccinimide (28 mg, 0.156 mmol), and triphenylphosphine (41 mg, 0.156 mmol). The mixture was heated to 50° C. and maintained at this temperature for an hour. The mixture was cooled down to rt. Methanol (0.5 mL) was added to destroy excess reagent. After 10 min, $Et_2O$ (25 mL) was added and the mixture was washed with $H_2O$ (10 mL), saturated $NaHCO_3$ (2×10 mL) and brine (10 mL). The organic layer was dried ($MgSO_4$), and concentrated in vacuo. The crude product was purified by Chromatotron (2 mm plate, 2% EtOAc in hexane) to afford Example 5 (12.5 mg, 42%) as a white solid. $^1$H NMR ($CDCl_3$) d 9.59 (s, 1H); 8.10 (s, 1H); 7.28 (d, 2H, J=8.5 Hz); 7.17 (d, 2H, J=8.1 Hz); 6.70 (bs, 1H); 4.59 (s, 2H); 3.82 (s, $OCH_3$); 2.34 (s, 3H); MS (FAB-LSIMS) 382, 384 [M+H]$^+$; m.p. 157–158° C.

Method E

Synthesis of 5-tert-Butyl-3-[3-(5-trifluoromethyl-[1,3,4]thiadiazol-2-yl)-ureido]-thiophene-2-carboxylic acid methyl ester. (Example 6)

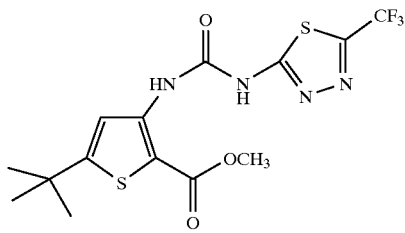

Step 1

To a solution of 20% phosgene in toluene (37.8 ml, 73.0 mmol) in dichloromethane (90 ml) at −15° C. was slowly added a solution of pyridine (5.9 ml, 73.0 mmol) and methyl 3-amino-5-tert-butyl thiophene-2-carboxylate (10.39 g, 48.7 mmol) in dichloromethane (60 ml). The reaction was allowed to slowly warm to 20° C. over 18 h. The resulting slurry was concentrated in vacuo to dryness and resuspended in ethyl ether and filtered with argon pressure through a glass frit. The solvent was removed in vacuo and the isocyanate residue was diluted to 0.2 M in toluene.

Step 2

A solution of 2-amino-5-trifluoromethyl-1,3,4-thiadiazole (84.5 mg, 500 umol) in 2 ml of the toluene solution from step 1 (400 umol) was stirred for 18 h and the solvent was removed in vacuo. The crude product was purified by flash chromatography with ethyl acetate/hexane affording 144.3 mg (88%) of Example 6 as a foam. $^1$H NMR ($CDCl_3$) d 12.5 (bs, 1H); 10.3 (s, 1H); 7.8 (s, 1H); 3.8 (s, 3H); 1.4 (s, 9H). FAB-MS (M+H)$^+$409.

5-tert-Butyl-3-[3-(1-methyl-1H-pyrazol-3-yl)-ureido]-thiophene-2-carboxylic acid methyl ester (example 9) was synthesized according to this procedure using N-methyl-3-amino-pyrazole in place of the 2-amino-5-trifluoromethyl-1,3,4-thiadiazole.

5-tert-Butyl-3-[3-(5-tert-butyl-[1,3,4]thiadiazol-2-yl)-ureido]-thiophene-2-carboxylic acid methyl ester (example 10) was synthesized according to this procedure using 2-amino-5-t-butyl-1,3,4-thiadiazole in place of the 2-amino-5-trifluoromethyl- 1,3,4-thiadiazole.

5-tert-Butyl-3-[3-(1H-indol-5-yl)-ureido]-thiophene-2-carboxylic acid methyl ester (example 11) was synthesized according to this procedure using 5-amino indole in place of the 2-amino-5-trifluoromethyl-1,3,4-thiadiazole.

5-tert-Butyl-3-[3-(5-methyl-thiazol-2-yl)ureido]-thiophene-2-carboxylic acid methyl ester (example 12) was synthesized according to this procedure using 2-amino-5-methyl thiazole in place of the 2-amino-5-trifluoromethyl-1,3,4-thiadiazole.

5-tert-Butyl-3-[3-(5-ethyl-[1,3,4]thiadiazol-2-yl)ureido]-thiophene-2-carboxylic acid methyl ester (example 13) was synthesized according to this procedure using 2-amino-5-ethyl-1,3,4-thiadiazole in place of the 2-amino-5-trifluoromethyl-1,3,4-thiadiazole.

5-tert-Butyl-3-[3-(5-methyl-[1,3,4]thiadiazol-2-yl)ureido]-thiophene-2-carboxylic acid methyl ester (example 14) was synthesized according to this procedure using 2-amino-5-methyl-1,3,4-thiadiazole in place of the 2-amino-5-trifluoromethyl- 1,3,4-thiadiazole.

5-tert-Butyl-3-[3-(5-cyclopropyl-[1,3,4]thiadiazol-2-yl)ureido]-thiophene-2-carboxylic acid methyl ester (example 15) was synthesized according to this procedure using 2-amino-5-cyclopropyl-1,3,4-thiadiazole in place of the 2-amino-5-trifluoromethyl-1,3,4-thiadiazole.

5-tert-Butyl-3-{3-[2-(1-methyl-1H-pyrrol-2-yl)-ethyl]ureido}-thiophene-2-carboxylic acid methyl ester (example 16) was synthesized according to this procedure using 2-(2-aminoethyl)-1-methyl-pyrrole in place of the 2-amino-5-trifluoromethyl-1,3,4-thiadiazole.

Method F

Synthesis of 5-tert-Butyl-3-[3-(4-methyl-thiophen-2-yl)ureido]-thiophene-2-carboxylic acid methyl ester. (Example 17)

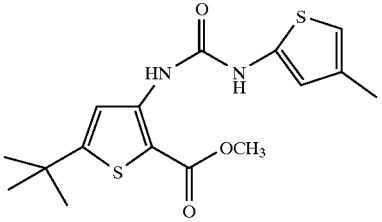

Step 1

A solution of 3-methylthiophene (5 ml, 51.75 mmol) and sodium persulfate (18.48 g, 77.6 mmol) and palladium acetate (5.81 g, 25.9 mmol) in acetic acid (500 ml) was heated to reflux. A slow stream of carbon monoxide was bubbled through the solution for 3 h. The reaction was cooled to 20° C. and concentrated in vacuo. The residue was dissolved in dichloromethane, celite was added and the solution was filtered and then passed through a pad of silica gel and concentrated in vacuo. The residue was dissolved in ethyl acetate and extracted into 2 N potassium hydroxide. The aqueous layer was washed with ethyl acetate and the pH was lowered to zero with HCl (conc.). The product was extracted into ethyl acetate, washed with saturated sodium chloride and concentrated in vacuo to yield 1.86 g (25%) of a mixture of 3-methyl-2-thiophene-carboxylic acid and 4-methyl-2-thiophene-carboxylic acid.

Step 2

A solution of 3-methyl-2-thiophene-carboxylic acid and 4-methyl-2-thiophene carboxylic acid (1.11 g, 7.81 mmol) and triethylamine (1.3 ml, 9.38 mmol) in acetone (75 ml) was cooled to −15° C. and ethyl chloroformate (1.12 ml, 11.72 mmol) was slowly added. The mixture was stirred for 15 min and sodium azide (863 mg, 13.28 mmol) in water (15 ml) was added. The reaction was stirred for 30 min, then diluted with dichloromethane and washed with 50% saturated sodium chloride. The organic phase was dried with magnesium sulfate and the solvent was removed in vacuo. The residue was purified by flash chromatography with hexane/ethyl acetate to give 913 mg (70%) of the mixture of azide esters.

Step 3

The azide ester (120 mg, 718 umol) was dissolved in toluene (3 ml) and heated to 100° C. for 5 h, then cooled to 20° C. Methyl 3-amino-5-tert-butyl-2-thiophene carboxylate (106 mg, 500 umol) was added and the reaction was heated to 95° C. for 18 h. The reaction was cooled to 20° C. and the solvent was removed in vacuo. The crude material was purified by flash chromatography with hexane/ethyl acetate and then purified by normal phase HPLC with dichloromethane, affording 82.1 mg (46%) of Example 17 and 18 mg (10%) of 3-methyl-thiophene derivative. $^1$H NMR (CDCl$_3$) 3-methyl derivative d 9.8 (s, 1H); 7.8 (bs, 2H); 6.55 (bs, 2H); 3.75 (s, 3H); 2.2 (s, 3H); 1.35 (s, 9H). FAB-MS (M+H)$^+$353.

5-tert-Butyl-3-(3-thiophen-2-yl-ureido)-thiophene-2-carboxylic acid methyl ester (example 7) was synthesized according to this procedure steps 2 and 3 using 2-thiophene carboxylic acid in place of 3-methyl-2-thiophene-carboxylic acid.

5-tert-Butyl-3-[3-(5-methyl-thiophen-2-yl)ureido]-thiophene-2-carboxylic acid methyl ester (example 8) was synthesized according to this procedure steps 2 and 3 using 5-methyl-2-thiophene carboxylic acid in place of 3-methyl-2-thiophene-carboxylic acid.

Method G

Synthesis of 5-tert-Butyl-3-[3-(1-ethyl-1H-pyrrol-3-yl)-ureido]-thiophene-2-carboxylic acid methyl ester. (Example 18)

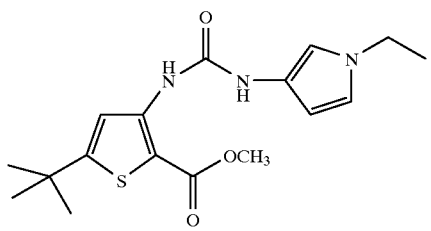

Step 1

A solution of 3-nitropyrrole (446 mg, 4.16 mmol), cesium carbonate (1.63 g, 4.99 mmol), iodoethane (998 ul, 12.48 mmol) in DMF (10 ml) was stirred for 2.5 hours at 20° C. The reaction was diluted with ethyl acetate, washed 1N hydrochloric acid (3×), dried with sodium sulfate and the solvent removed in vacuo. The crude material was purified by flash chromatography with 100% dichloromethane affording 480 mg (82%) as an oil.

Step 2

To a solution of the product from Step 1 (480 mg, 3.43 mmol) in methanol (10 ml) was added 10% palladium on charcoal (30 mg). The reaction was hydrogenated at atmospheric pressure for 18 h at 20° C., then filtered. The solvent was removed in vacuo affording 342 mg (91%) as a oil.

Step 3

A solution of the product from Step 2 (342 mg, 3.11 mmol) and methyl-5-t-butyl-3-isocyanothiophene-2-carboxylate (0.2 M in toluene, 3 ml) was stirred for 20 h at 20° C. The solvent was removed in vacuo and the crude material was purified by flash chromatography with ethyl acetate/hexane affording 136 mg (65%) of Example 18 as a foam. $^1$H NMR (CDCl$_3$) d 9.7 (s, 1H); 8.0 (s, 1H); 7.75 (s, 1H); 7.65 (m, 2H); 7.3 (m, 2H); 3.8 (s, 3H); 1.3 (s, 9H). FAB-MS (M+H)$^+$350.

5-tert-Butyl-3-[3-(1-propyl-1H-pyrrol-3-yl)-ureido]-thiophene-2-carboxylic acid methyl ester (example 19) was synthesized according to this procedure using allyl bromide in place of the iodoethane.

5-tert-Butyl-3-[3-(1-isopropyl-1H-pyrrol-3-yl)-ureido]-thiophene-2-carboxylic acid methyl ester (example 20) was synthesized according to this procedure using 2-bromopropane in place of the iodoethane.

5-tert-Butyl-3-[3-(1-ethyl-1H-pyrazol-3-yl)-ureido]-thiophene-2-carboxylic acid methyl ester (example 21) was synthesized according to this procedure using 3-nitropyrazole in place of the 3-nitropyrrole.

Method H

Synthesis of 5-tert-Butyl-3-(3-p-tolyl-ureido)-furan-2-carboxylic acid methyl ester. (Example 22)

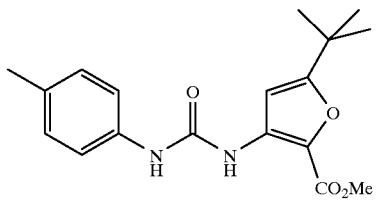

Step 1 n-Butyllithium (25 mL, 40 mmol, 1.6 M in hexane solution, 1.1 equiv) is added dropwise to a solution of 4.5 g of 2-t-butylfuran (36 mmol) in 60 mL of dry THF at −78° C. under N$_2$. After 30 min, the cooling bath is replaced with an ice bath and the mixture stirred at 0° C. for 1 h. Dry CO$_2$, generated from dry ice and dried over an anhydrous Na$_2$SO$_4$ tower, is bubbled into the reaction mixture over 20 min at −78° C. and then at 0° C. The reaction mixture is acidified with 1 M HCl to pH 1, then extracted with ethyl acetate. The organic layer is washed with brine, dried (NaSO$_4$) and concentrated to give 4.2 g of 2-tertbutyl 5-furanoic acid as a pale yellow solid (69%). $^1$H NMR (CDCl$_3$) d 11.0 (br s, 1H), 7.19 (d, 1H, J=3.3 Hz), 6.11 (d 1H, J=3.3 Hz), 1.29 (s, 9H).

Step 2

A solution of 2.0 g of the furanoic acid (11.9 mmol) in 30 mL of dry THF is cooled to −78° C. under N$_2$ before the dropwise addition of 15.6 mL of n-butyllithium (25 mmol, 1.6 M in hexane solution, 2.1 equiv). After 30 min, 2.3 g of TsN$_3$ (11.9 mmol, 1.1 equiv) in 3 mL of dry THF (3 mL wash) is added dropwise via cannula. The yellow solution is allowed to heat to 0° C. over 2 h, then 6 g of potassium acetate (60 mmol, 5 equiv) is added and the suspension is stirred rapidly at rt for 14 h. The mixture is diluted with ether and extracted with water. The aqueous phase is acidified to pH 1 with 1 M HCl, then extracted thoroughly with ethyl acetate. The organic phase is washed further with brine, dried over NaSO$_4$ and concentrated. A hexane solution of TMSCHN$_2$ (45 mL, 90 mmol, 2.0 M) is added to the red oil in 150 mL of ether and 20 mL of methanol. After 30 min, the mixture is concentrated, and subjected to flash chromatography (10% ethyl acetate in hexane) to give 1.72 g of a colorless oil. Analysis of the product by $^1$HNMR indicates a ~2:3 mixture of the title compound and 5-t-butyl-2-furanoic acid methyl ester, which co-elute. The mixture is used without further purification. FTIR (film) cm$^{-1}$ 2965 (s), 2118 (s), 1723 (s); $^1$H NMR (CDCl$_3$) d 5.99 (s, 1H), 3.80 (s, 3H), 1.25 (s, 9H).

Step 3

A Parr bottle containing 1.72 g of the mixture obtained from the above reaction and 0.5 g of Pd (10% on carbon) in 30 mL of cellosolve is successively evacuated and purged with H$_2$ gas three times. The reaction mixture is then shaken under an atmosphere of H$_2$ (40 psi) for 1 h, diluted with ethyl acetate and filtered through celite. The concentrated solution is flash chromatographed (20% ethyl acetate in hexane) to give 0.59 g of the amine (25% total yield) as a crystalline solid as well as 0.73 g of recovered methyl ester (34%). FTIR (film) cm$^{-1}$ 3330–2950 (s, br), 2850 (m), 1680 (s), 1637 (s), 1537 (s), 1346 (s), 1131 (s); $^1$H NMR (CDCl$_3$) d 5.76 (s, 1H), 4.24 (br s, 2H), 1.29 (s, 9H); $^{13}$C NMR (CDCl$_3$) d 178.7, 168.1, 160.5, 144.9 (br), 124.1, 98.3, 50.5, 32.8, 28.3.

Step 4

Phosgene (1.3 mL, 2.5 mmol, 1.93 M solution in toluene, 10 equiv) is added rapidly to a solution of 50 mg of the product from step 3 (0.25 mmol) in 1.0 mL of dry pyridine and 5 mL of dry toluene at rt under N$_2$. After 30 min, the orange suspension is concentrated in vacuo, then successively charged with 1 mL of dry toluene and evaporated (2 times). Finally, 3 mL of toluene is added before the addition of 100 mg of toluidine (0.93 mmol, 3.7 equiv). The orange mixture is stirred overnight, diluted with ethyl acetate and washed with 1 M HCl, and brine, then dried (Na$_2$SO$_4$) and concentrated. The residue is purified by flash chromatography to give 80 mg of Example 22 (96%) as a pale yellow oil. FTIR (film) cm$^{-1}$ 3400–3200 (m, br), 2966 (s), 1676 (s), 1622 (s), 1536 (s), 1306 (s), 1097 (m); $^1$H NMR (CDCl$_3$) d 8.68 (br s, 1H), 7.87 (br s, 1H), 7.27 (d, 2H, J=8.1 Hz), 7.11 (d, 2H, J=8.1 Hz), 7.02 (s, 1H), 3.77 (s, 3H), 2.30 (s, 3H), 1.28 (s, 9H); $^{13}$C NMR (CDCl$_3$) d 168.2, 160.5, 152.5, 137.7, 134.8, 134.0, 129.5, 126.0, 121.4, 100.1, 51.0, 33.0, 28.3, 20.6.

5-tert-Butyl-3-[3-(3,4-dichloro-phenyl)-ureido]-furan-2-carboxylic acid methyl ester (example 23) was synthesized according to this procedure using amino-3,4-dichlorobenzene in place of the toluidine.

Method I

Synthesis of 5-tert-Butyl-3-(3-p-tolyl-ureido)-1H-pyrrole-2-carboxylic acid methyl ester. (Example 24)

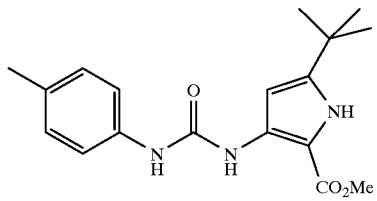

Step 1

Chlorotrimethylsilane (17.9 mL, 141 mmol, 2.5 equiv) is added in one portion to a solution of pyrrole-2-carboxylic acid (6.28 g, 56.5 mmol) in dry methanol (100 mL) under N$_2$ at rt. After stirring overnight, the reaction mixture is concentrated in vacuo, redissolved in dichloromethane, washed with water, dried (Na$_2$SO$_4$) and concentrated to give 4.62 g of methyl pyrrole-2-carboxylate as a tannish semi-crystalline solid (65%), which was used without further purification. $^1$H NMR (CDCl$_3$) d 9.3 (br s, 1H), 6.96 (br m, 1H), 6.92 (br m, 1H), 6.29 (br q, 1H), 3.86 (s, 3H).

Step 2

Aluminum chloride (0.710 g, 5.33 mmol, 2.2 equiv) is added in one portion to a solution of methyl pyrrole-2-carboxylate (0.30 g, 2.42 mmol) in dry dichloroethane (12 mL) under N$_2$ at rt. Subsequently, 2-chloro-2-methylpropane (0.26 mL, 2.42 mmol, 1.0 equiv) is added in one portion via syringe. After 2 h, the orange solution is quenched by slowly pouring into a saturated sodium bicarbonate solution. The resulting white suspension is extracted with diethyl ether (2×). The combined organic layers are dried (Na$_2$SO$_4$) and concentrated in vacuo to give 0.40 g of methyl 5-t-butylpyrrole-2-carboxylate as an off-white solid. Flash chromatography (40% hexane in dichloromethane) gives 0.3 6 g of the desired material as a white amorphous solid (81%). $^1$H NMR (CDCl$_3$) d 8.82 (br s, 1H), 6.81 (t, 1H, J=3.3 Hz), 6.00 (t, 1H, J=3.3 Hz), 3.83 (s, 3H), 1.31 (s, 9H).

Step 3

Fuming nitric acid (0.57 mL, 13.6 mmol, 1.5 equiv) is added in one portion via syringe to a heterogeneous mixture of methyl-5-t-butylpyrrole-2-carboxylate (1.65 g, 9.10 mmol) in concentrated sulfuric acid (19 mL) under N$_2$ at rt. After 1 h, the reaction is poured over ice-water and slowly neutralized to pH 7 with solid sodium carbonate, extracted with diethyl ether (2×), dried (Na$_2$SO$_4$), and concentrated in vacuo. The residue is subjected to flash chromatography (30% hexane in dichloromethane) to give 0.44 g of the desired product, in addition to 0.27 g of bis-nitrated product which has higher mobility. Rechromatographing of mixed fractions provides a further 0.22 g of methyl 5-t-butyl-3-nitropyrrole-2-carboxylate (32% total yield). Mono-nitrated: $^1$H NMR (CDCl$_3$) d 9.22 (br s, 1H), 6.56 (d, 1H, J=3.3 Hz), 3.93 (s, 3H), 1.33 (s, 9H). Bis-nitrated: $^1$H NMR (CDCl$_3$) d 9.17 (br s, 1H), 3.91 (s, 3H), 1.52 (s, 9H).

Path A

Step 4

A Parr hydrogenation bottle fitted with a 16×100 mm disposable glass culture tube is charged with methyl-5-t-butyl-3-nitropyrrole-2-carboxylate (14 mg, 0.062 mmol) in dry methanol (1 mL) and Pd (10% on carbon, 3 mg). The reaction is successively evacuated and purged with H$_2$ gas three times. The reaction mixture is then shaken under an atmosphere of H$_2$ (35 psi) for 1 h, diluted with dichloromethane and filtered through celite. The filtrate is concentrated in vacuo to give methyl 3-amino-5-t-butylpyrrole-2-carboxylate as a bright yellow oil (100%, crude yield). $^1$H NMR (CDCl$_3$) d 7.89 (br s, 2H), 5.52 (d, 1H, J=2.8 Hz), 3.82 (s, 3H), 1.26 (s, 9H).

Step 5

Phosgene (0.32 mL, 0.62 mmol, 1.93 M solution in toluene, 10 equiv) is added rapidly to a solution of methyl-3-amino-5-t-butylpyrrole-2-carboxylate (12.2 mg, 0.062 mmol) and dry pyridine (247 mL, 3.06 mmol, 49.4 equiv) in dry toluene (1 mL). After 30 min, the orange suspension is concentrated in vacuo, then successively charged with 1 mL of dry toluene and evaporated (2×). Finally, toluene (2 mL) is added before the addition of p-toluidine (10 mg, 0.094 mmol). The mixture is heated at for 3 h before being concentrated in vacuo. The residue is purified by preparative TLC (2 plates, 0.25 mm thick, 20×20 cm, 2% methanol in dichloromethane). The major UV active band is isolated and the product is extracted with 5% methanol in dichloromethane to give 16.4 mg of Example 24 as a pale yellow amorphous solid (80%). FT-IR (KBr pellet) cm$^{-1}$ 3341 (s), 2947 (m), 1676 (s), 1583 (s), 1548 (s), 1456 (s), 1279 (s), 1208 (s), 1094 (s); MS (ES)=330.1 (m+1); $^1$H NMR (MeOD, CDCl$_3$) d 8.45 (br s, 1H), 8.19 (br s, 1H), 7.27 (d, 2H, J=7.3 Hz), 7.14 (d, 2H, J=8.4 Hz), 6.95 (br s, 1H), 6.78 (d, 1H, J=2.8 Hz), 3.73 (s, 3H), 2.32 (s, 3H), 1.29 (s, 9H); $^{13}$C NMR (MeOD, CDCl$_3$) d 161.89, 153.51, 147.62, 136.15, 132.17, 128.90, 119.58, 105.92, 97.36, 50.00, 31.45, 28.99, 19.65.

Synthesis of 5-tert-Butyl-1-methyl-3-(3-p-tolyl-ureido)-1H-pyrrole-2-carboxylic acid methyl ester. (Example 25)

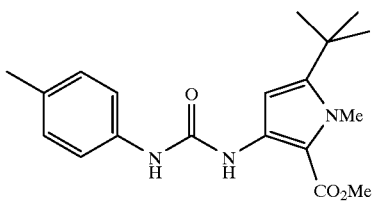

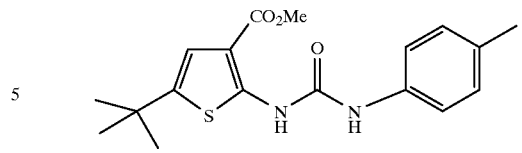

Path B
Step 6

Sodium hydroxide (0.21 g, 2.65 mmol, 50% aqueous, 6 equiv) is added to a cold (0–−10° C.) solution of methyl 5-t-butyl-3-nitropyrrole-2-carboxylate (100 mg, 0.44 mmol), benzyltributyl ammonium bromide (158 mg, 0.44 mmol, 1 equiv), and dimethyl sulfate (46 mL, 0.49 mmol, 1.1 equiv) in dichloromethane (1 mL). After 5 min, the cooling bath is removed and the mixture is stirred for 4 h at rt. The reaction mixture is diluted with dichloromethane, washed with water (1×), 10% ammonium acetate (2×), dried ($Na_2SO_4$), and concentrated in vacuo to give a bright yellow oil. The residue is purified by flash chromatography (30% hexane in dichloromethane) to give 61 mg of methyl 5-t-butyl-1-methyl-3-nitropyrrole-2-carboxylate as a pale yellow oil which solidifies upon standing (62%). $^1$H NMR ($CDCl_3$) d 6.47 (s, 1H), 3.92 (s, 3H), 3.80 (s, 3H), 1.38 (s, 9H).

Step 7

The nitro compound is reduced in a similar manner to that for methyl 3-amino-5-t-butylpyrrole-2-carboxylate to give 59 mg of methyl 3-amino-1-methyl-5-t-butylpyrrole-2-carboxylate as an oil (100%, crude yield). $^1$H NMR ($CDCl_3$) d 5.48 (s, 1H), 4.34 (br s, 2H), 3.85 (s, 3H), 3.80 (s, 3H), 1.33 (s, 9H). $^{13}$C NMR ($CDCl_3$) d 162.24, 148.95, 142.27, 107.39, 95.73, 50.55, 50.04, 34.73, 31.92, 29.67.

Step 5

Phosgene (1.45 mL, 2.80 mmol, 1.93 M solution in toluene, 10 equiv) is added rapidly to a solution of methyl-3-amino-1-methyl-5-t-butylpyrrole-2-carboxylate (59 mg, 0.280 mmol) in dry pyridine (1 mL) and dry toluene (2 mL). Additional dry toluene (3 mL) is added to aid stirring of the heterogeneous mixture. After 30 min, the orange suspension is concentrated in vacuo, then successively charged with dry toluene (1 mL) and evaporated (2×). Finally, toluene (3 mL) is added before the addition of p-toluidine (111 mg, 1.04 mmol, 3.7 equiv). The resulting homogeneous mixture is stirred overnight, diluted with dichloromethane and washed with 1 M HCl. The aqueous layer was thoroughly back-extracted with dichloromethane (2×) and the combined organic phases are dried ($Na_2SO_4$), concentrated in vacuo, and purified by flash chromatography (10% Æ 25% ethyl acetate in hexane) to give 66 mg of the Example 25 as a pale yellow solid (69%). FT-IR (KBr pellet) $cm^{-1}$ 2364 (s), 2335 (s), 1659 (m), 1579 (m), 1542 (m), 1354 (w), 1232 (w); $^1$H NMR ($CDCl_3$) d 8.81 (br s, 1H), 7.26 (ap d, 3H (2H+1 NH), J=8.4 Hz), 7.11 (d, 2H, J=8.4 Hz), 6.80 (s, 1H), 3.88 (s, 3H), 3.64 (s, 3H), 2.31 (s, 3H), 1.35 (s, 9H); $^{13}$C NMR ($CDCl_3$) d 161.95, 153.01, 148.59, 135.34, 133.97, 133.78, 129.54, 122.02, 108.82, 98.76, 50.38, 35.03, 32.12, 31.37, 29.76.

Method J

Synthesis of 5-tert-Butyl-2-(3-p-tolyl-ureido)-thiophene-3-carboxylic acid methyl ester. (Example 26)

Step 1

Triethyl amine (3.04 mL, 21.8 mmol) was added to a solution of methyl cyanoacetate (4.00 g, 40.4 mmol), sulfur (1.29 g, 40.4 mmol) and DMF (20 mL) at ambient temperature. 3,3-dimethyl butraldehyde (5.08 g, 40.4 mmol) was added and stirred 1 h before being poured into water (200 mL). Solids were filtered off and filtrate was extracted with ethyl acetate. The acetate layer was filtered through a plug of silica gel and concentrated in vacuo. Purification via flash chromatography afforded 4.19 g (49%) of methyl 2-amino-5-t-butylthiophene 3-carboxylate.

Step 2

Methyl 2-amino-5-t-butylthiophene 3-carboxylate was then condensed with p-tolyl isocyanate under conditions described in Method A, Step 2 to produce 29.4 mg of Example 26 (18.1%). $^1$H NMR ($CDCl_3$) d 10.37 (s, 1h); 7.32 (d, J=8.5 Hz, 2H); 7.16 (d, J=8.1 Hz, 2H); 6.82 (s, 1H); 6.75 (bs, 1h); 3.81 (s, 3H); 2.34 (s, 3H); 1.38 (s, 9H); mp 109–111° C.

5-tert-Butyl-2-(3-phenyl-ureido)-thiophene-3-carboxylic acid methyl ester (example 27) was synthesized according to this method using phenyl isocyanate in place of the p-tolyl isocyanate.

5-tert-Butyl-2-(3-(5-ethyl-[1,3,4]thiadiazol-2-yl)-ureido)-thiophene-3-carboxylic acid methyl ester (example 28) was synthesized according to this method step 1 then Method E using 2-amino-5-ethyl-1,3,4-thiadiazole in place of the 2-amino-5-trifluoromethyl-1,3,4-thiadiazole.

5-Isopropyl-2-(3-p-tolyl-ureido)-thiophene-3-carboxylic acid methyl ester (example 29) was synthesized according to this method step 1 using 3-methyl butraldehyde in place of 3,3-dimethyl butraldehyde followed by Method E using toluidine in place of the 2-amino-5-trifluoromethyl-1,3,4-thiadiazole.

5-Isopropyl-2-[3-(5-methyl-thiophen-2-yl)-ureido]-thiophene-3-carboxylic acid methyl ester (example 30) was synthesized according to this method step 1 using 3-methyl butraldehyde in place of 3,3-dimethyl butraldehyde followed by Method F steps 2 and 3 using 5-methyl-2-thiophene carboxylic acid in place of 3-methyl-2-thiophenecarboxylic acid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of cancerous cell growth mediated by raf kinase, comprising administering a compound of the formula:

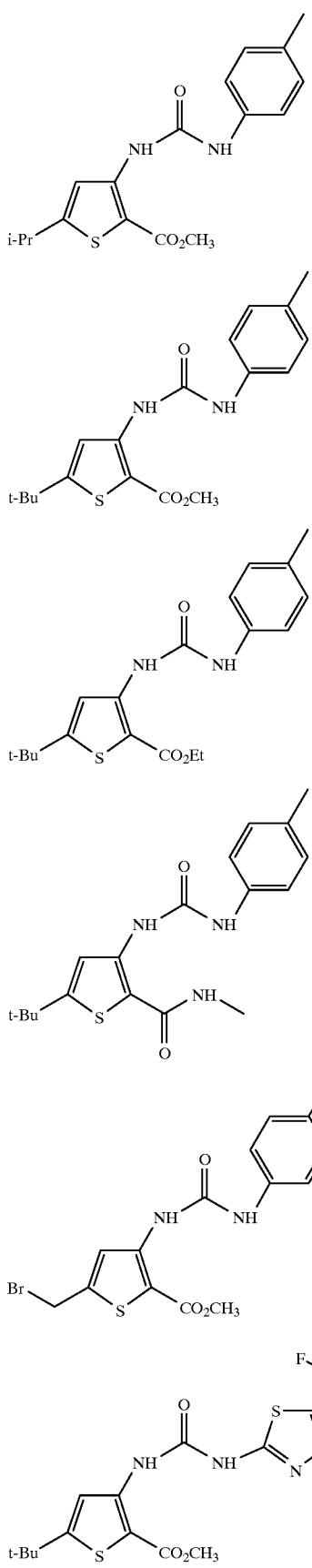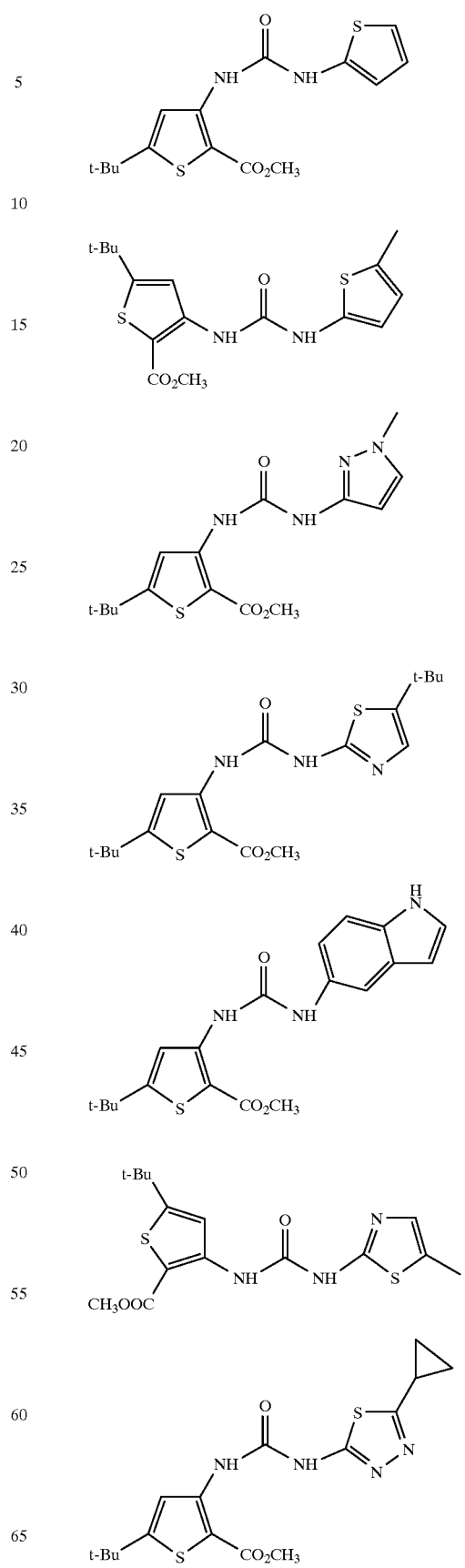

-continued
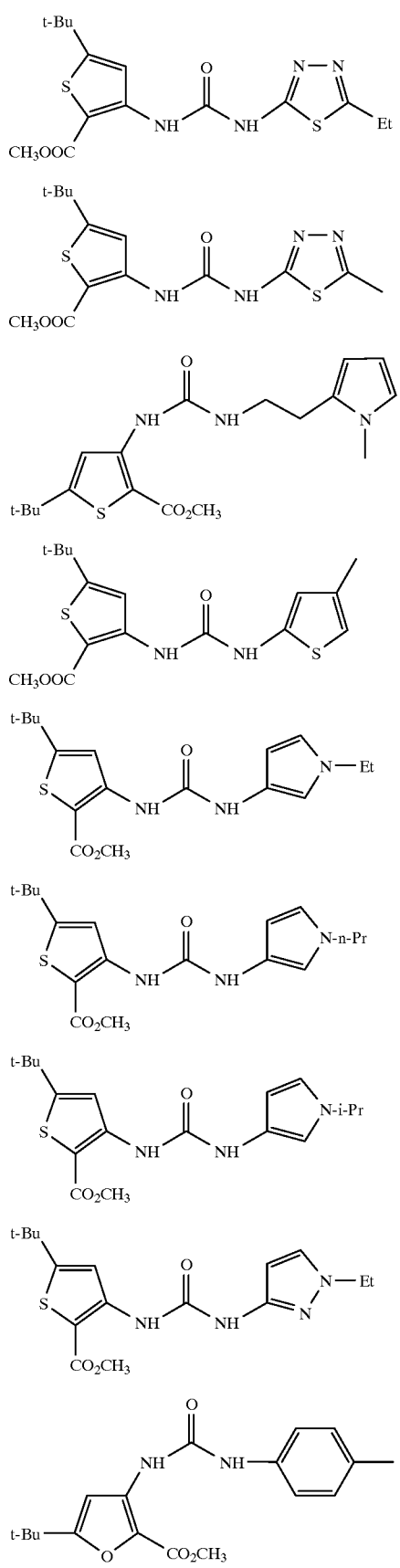
-continued
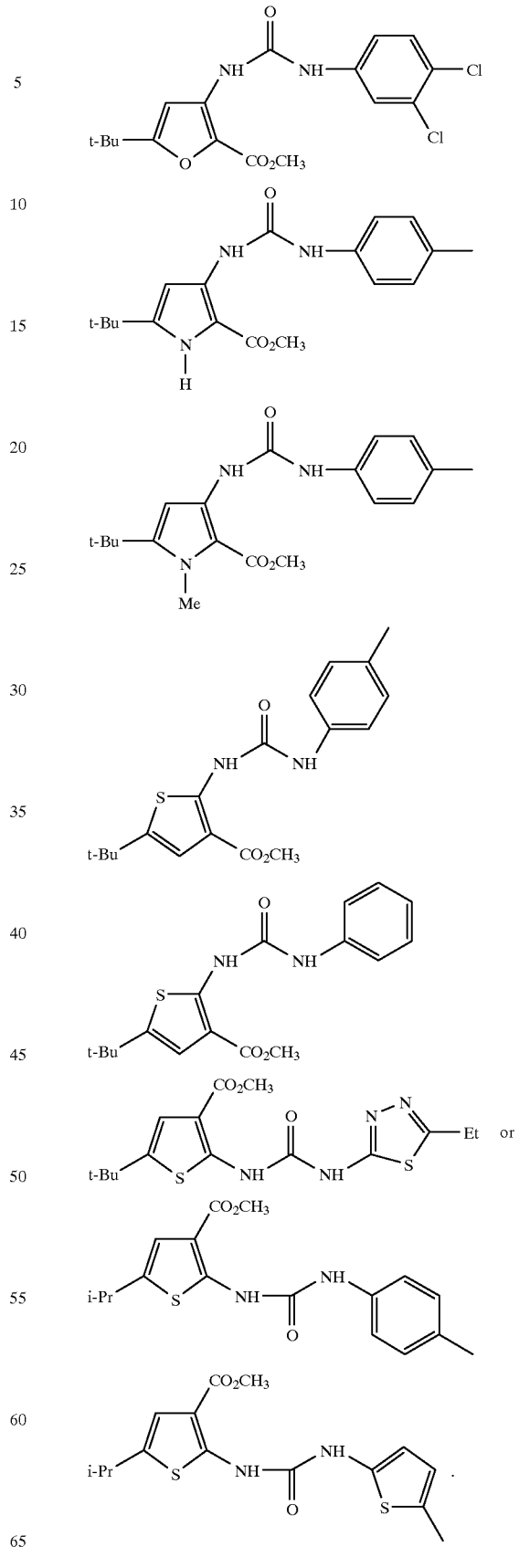

2. A method according to claim 1, comprising administering a compound of the formula
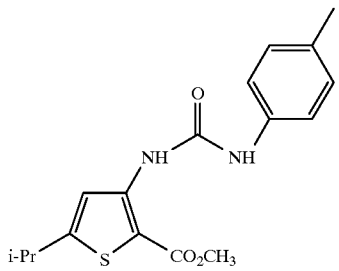
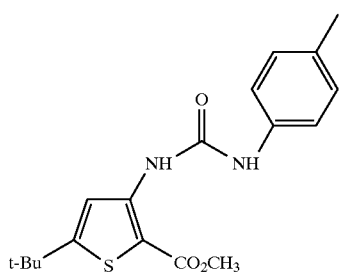
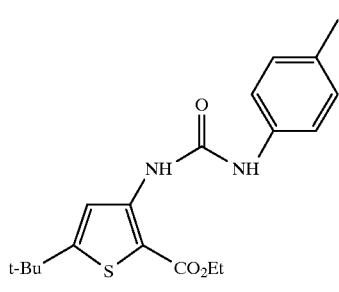
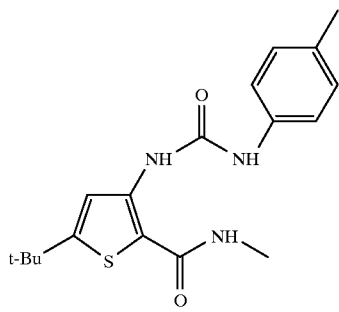
or
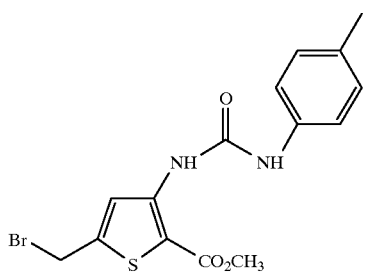
3. A method according to claim 1, comprising administering a compound of the formula
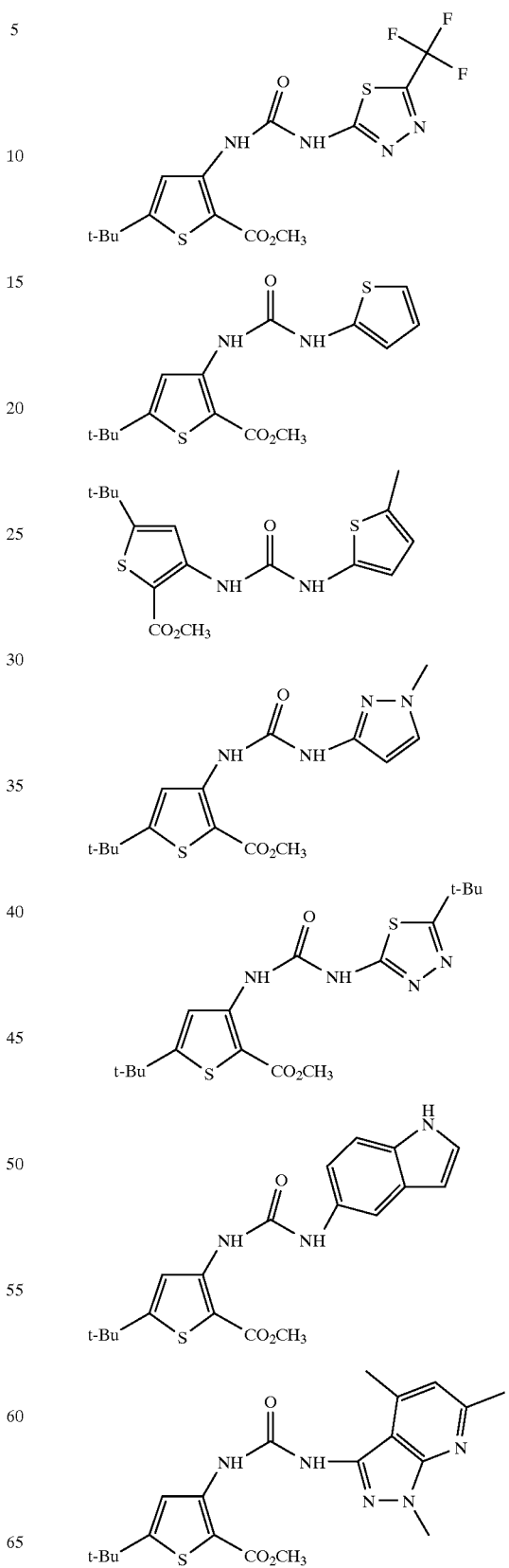

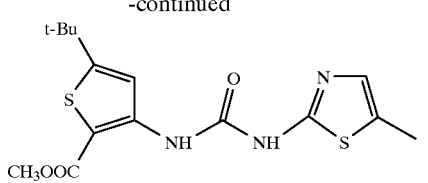
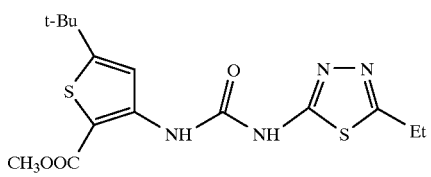
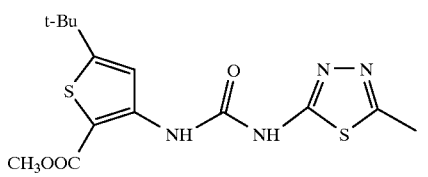
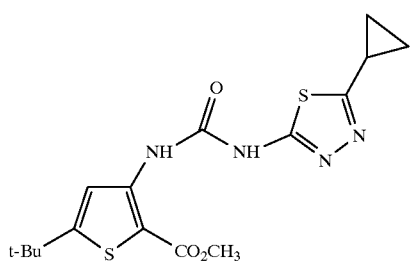
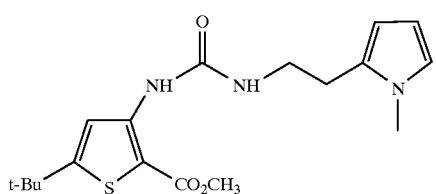
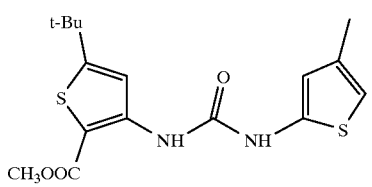
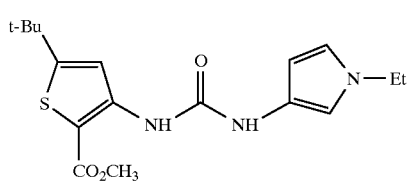
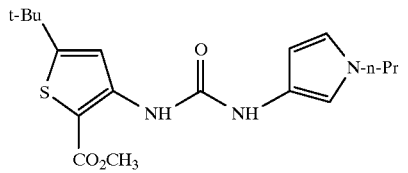
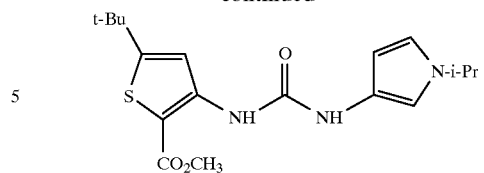
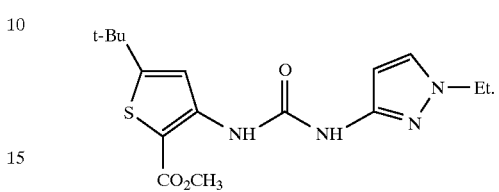
4. A method according to claim 1, comprising administering a compound of formula
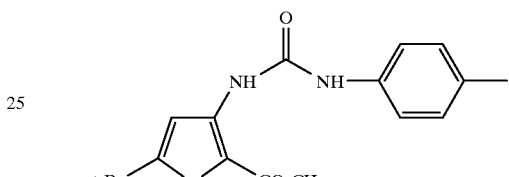
or
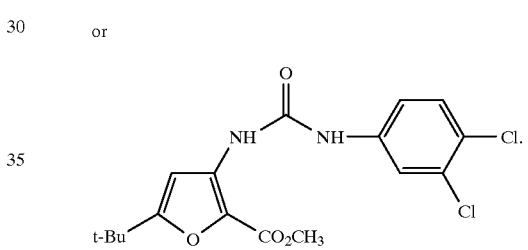
5. A method according to claim 1, comprising administering a compound of formula
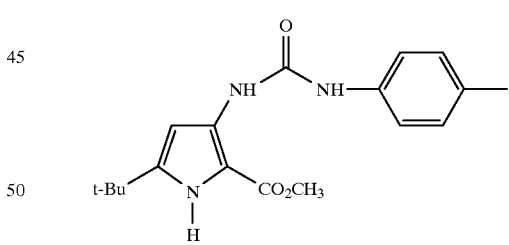
or
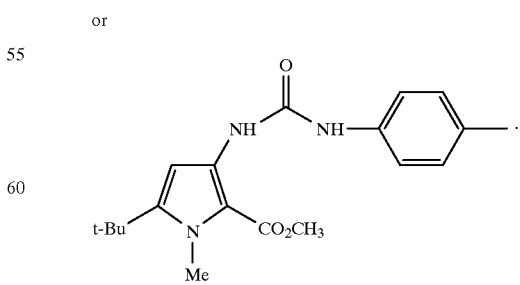
6. A method according to claim 1, comprising administering a compound of formula

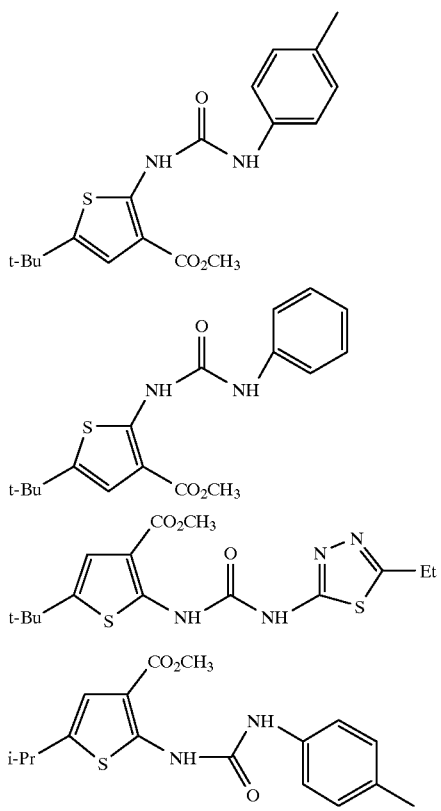
or
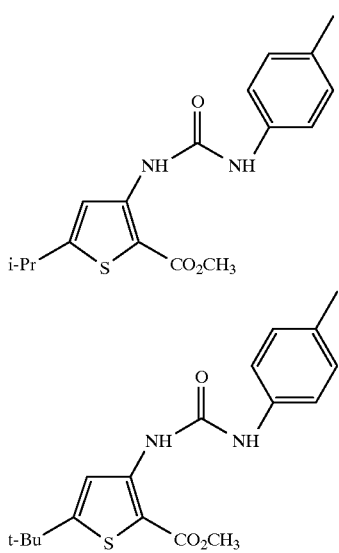
7. A method according to claim 1, comprising administering a compound of formula
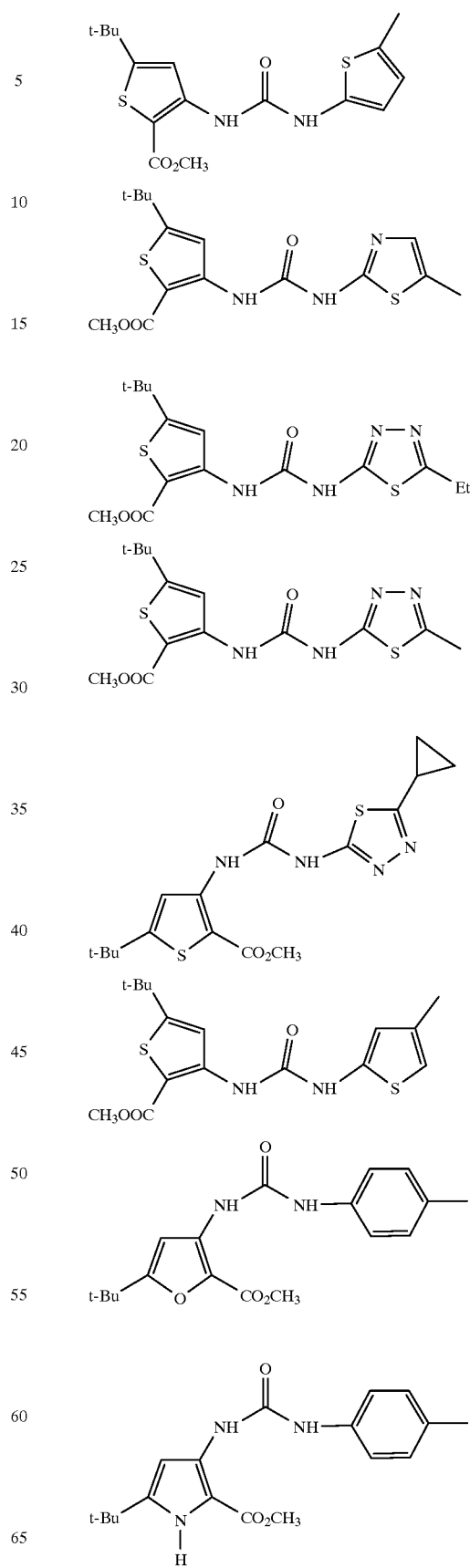

-continued
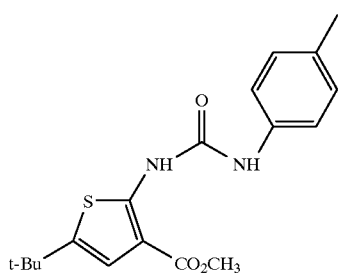
or
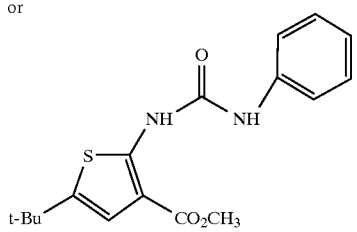
8. A compound of the formula
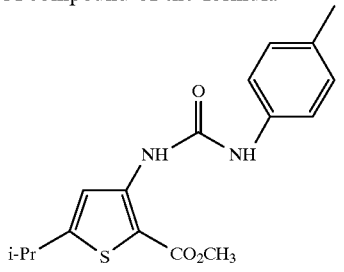
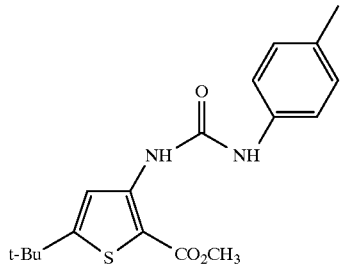
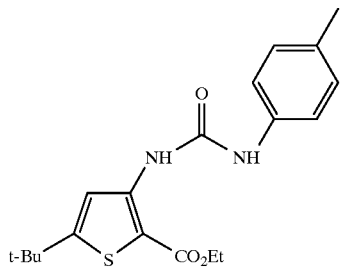
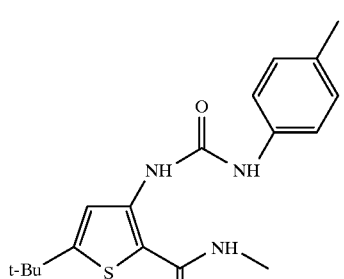
-continued
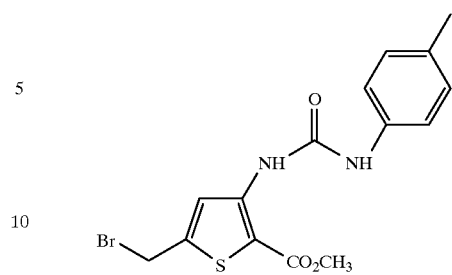
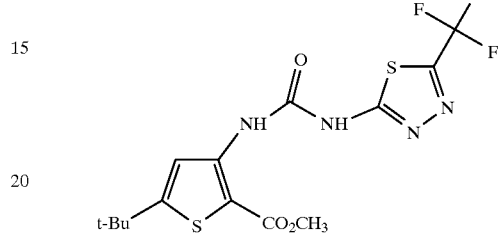
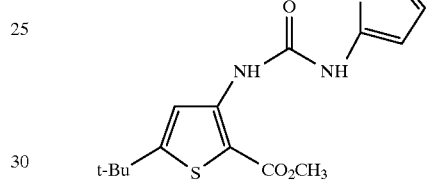
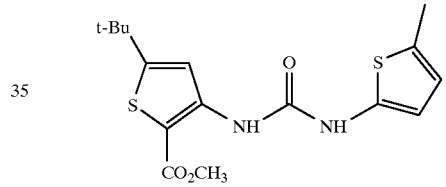
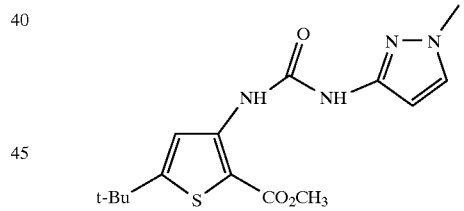
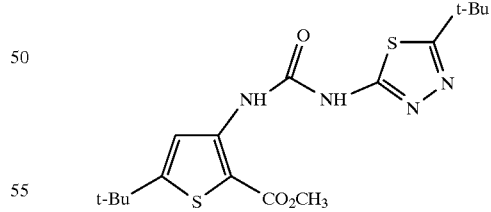
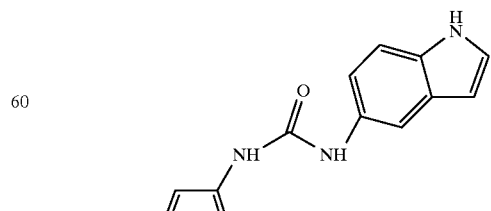

-continued
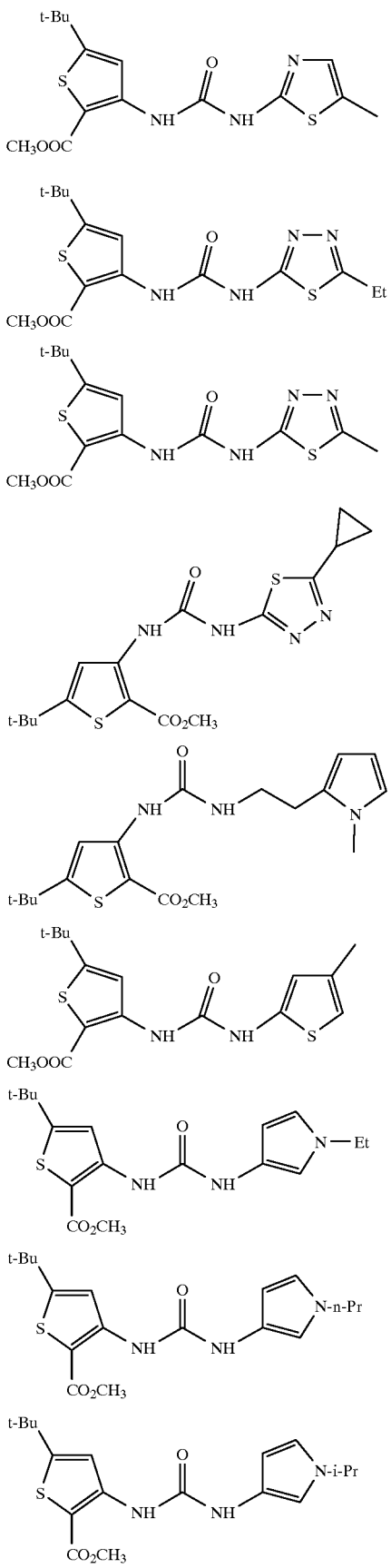
-continued
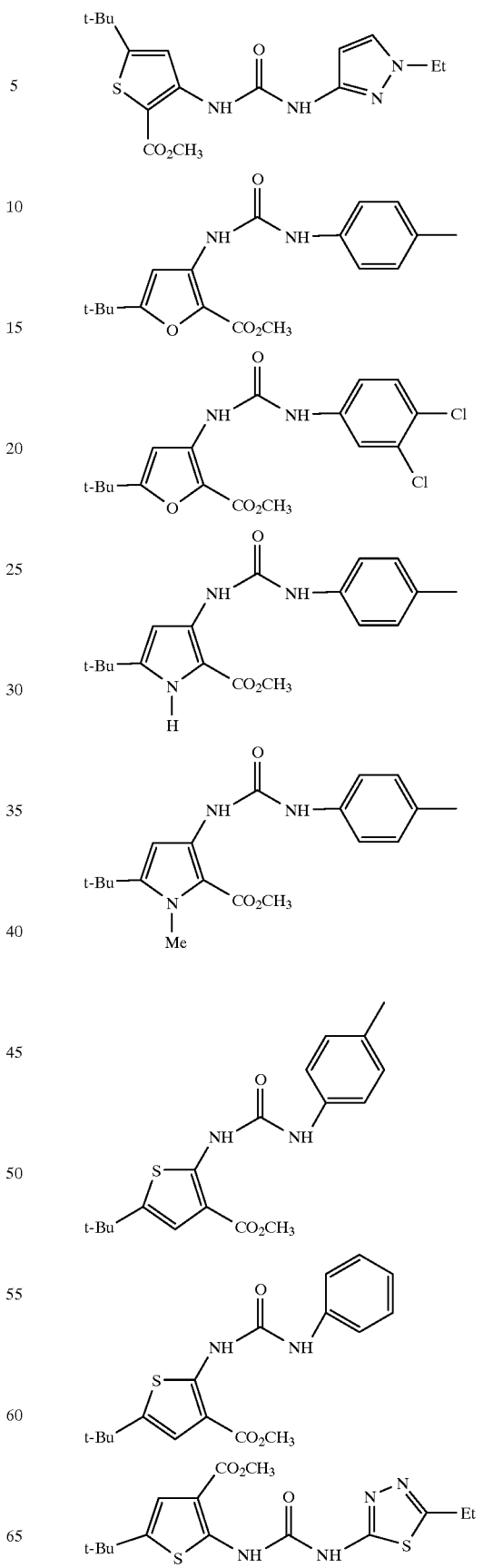

-continued
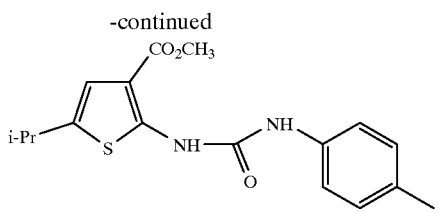
or
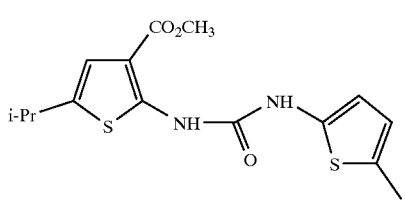
9. A compound according to claim 8, of the formula
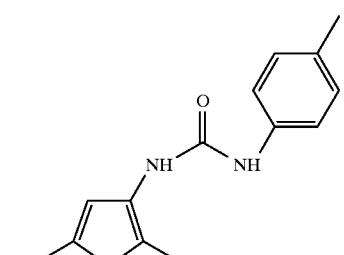
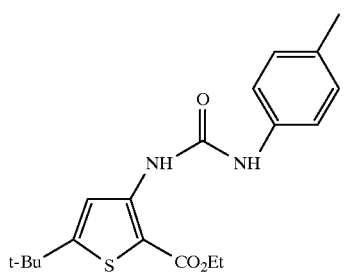
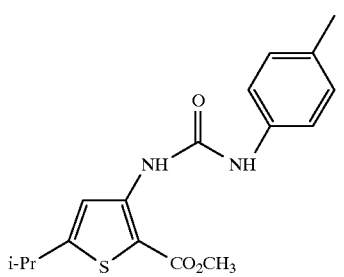
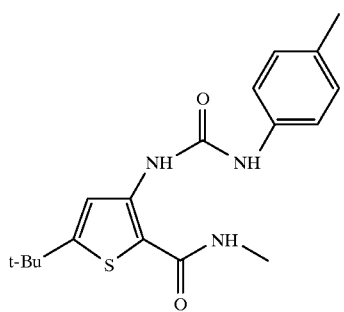
-continued
or
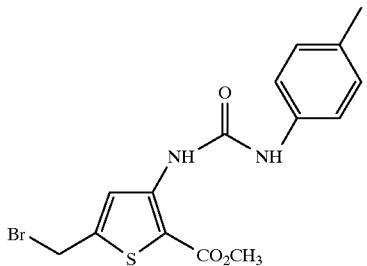
10. A compound according to claim 8, of the formula
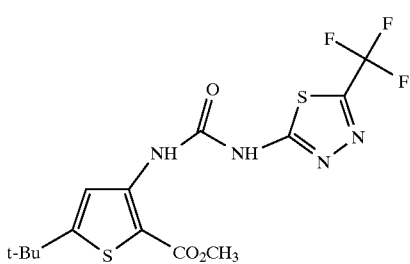
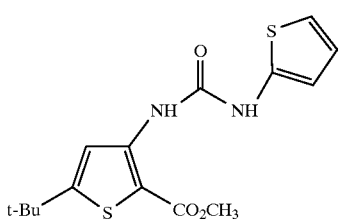
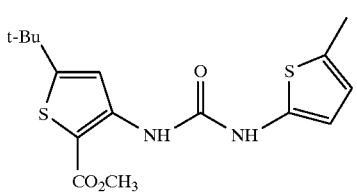
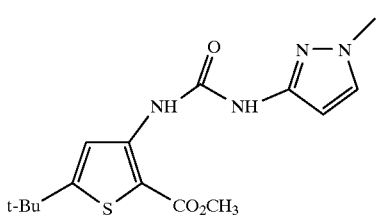
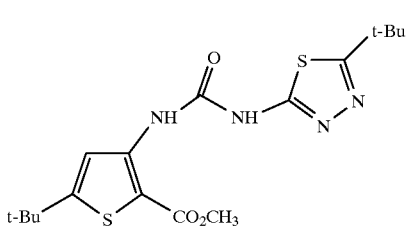

-continued
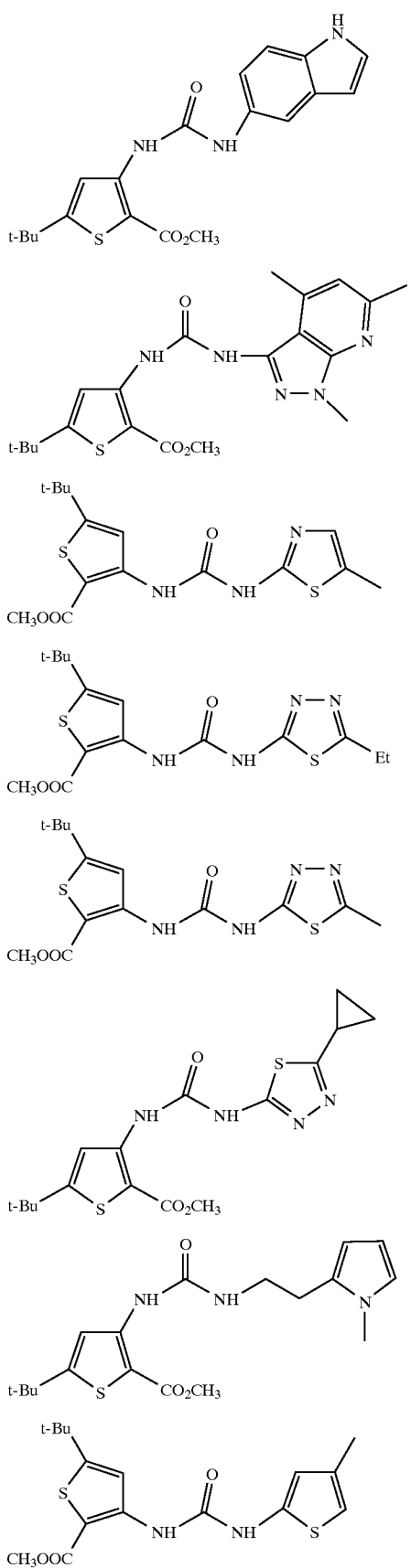
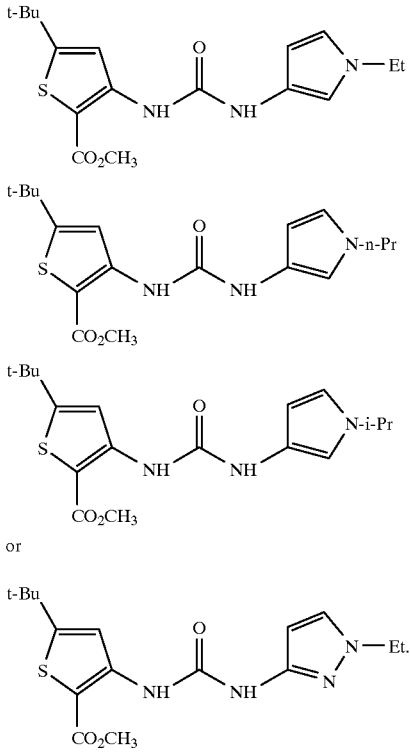
11. A compound according to claim 8, of the formula
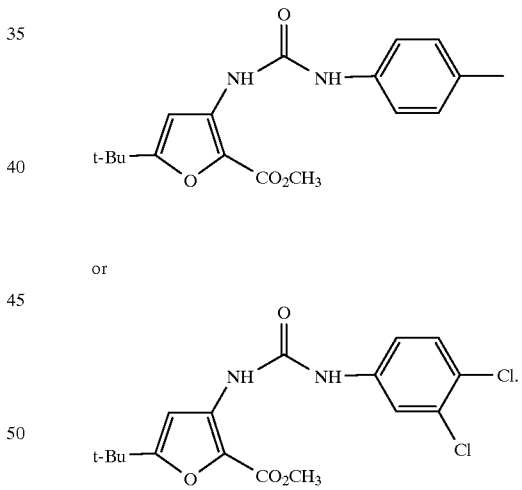
or
12. A compound according to claim 8, of the formula
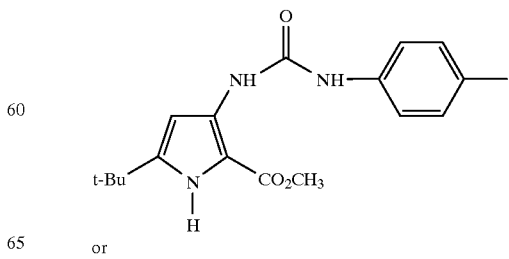
or -continued
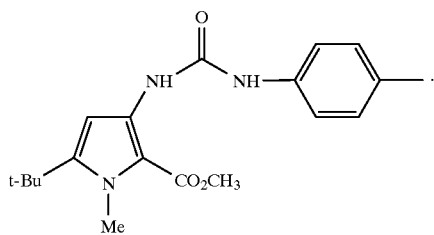
13. A compound according to claim 8, of the formula
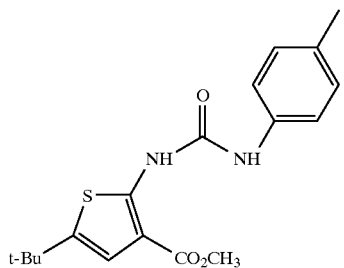
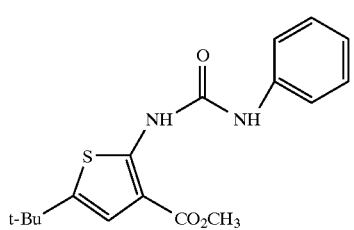
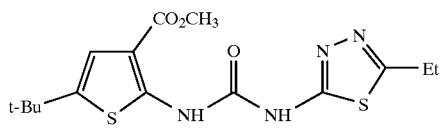
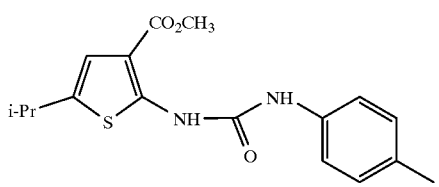
or
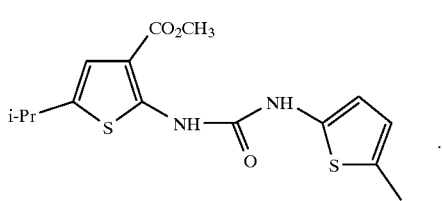
14. A compound according to claim 8, of the formula
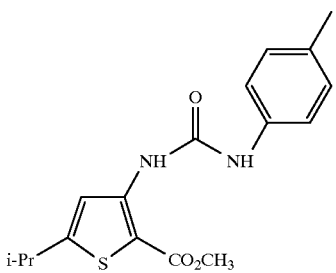
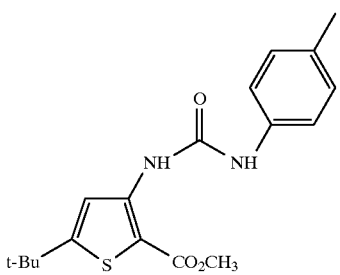
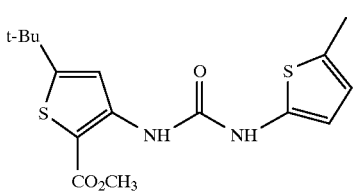
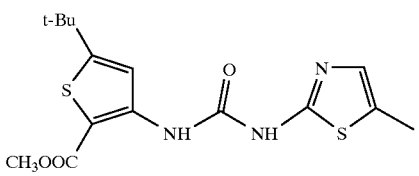
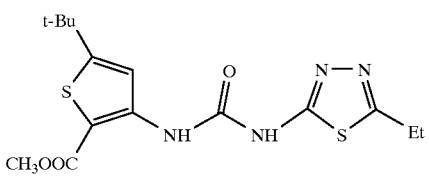
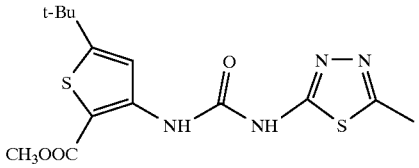
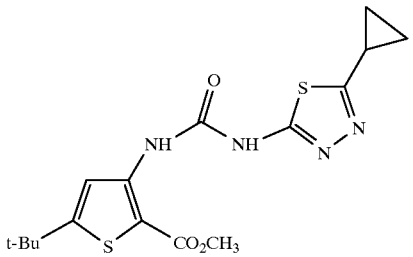

-continued

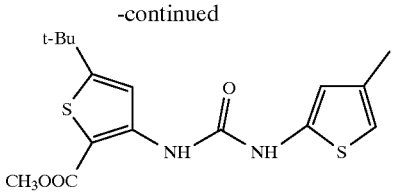

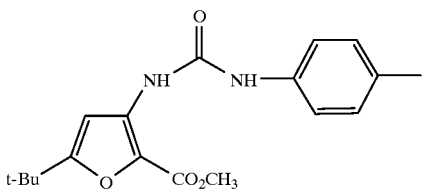

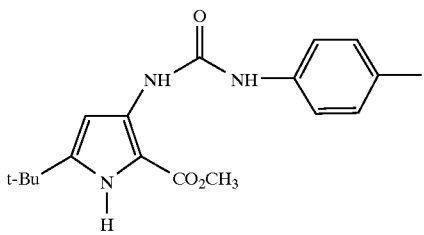

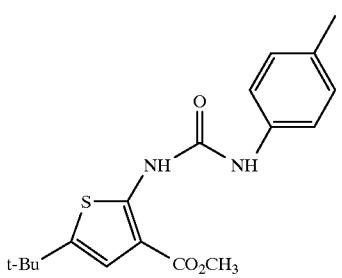

or

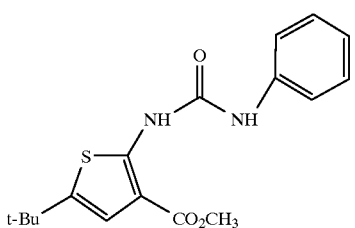

15. A pharmaceutical composition comprising a compound according to claim 8 and a physiologically acceptable carrier.

16. A pharmaceutical composition comprising a compound according to claim 14 and a physiologically acceptable carrier.

17. A pharmaceutical composition comprising a compound according to claim 8 and a physiologically acceptable carrier, in sterile form.

18. A compound of the formula

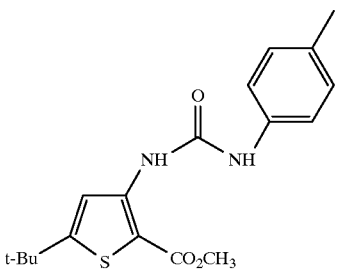

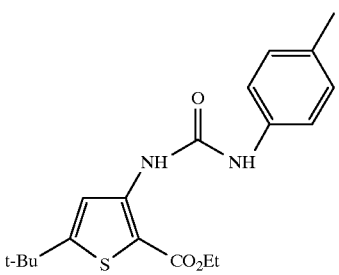

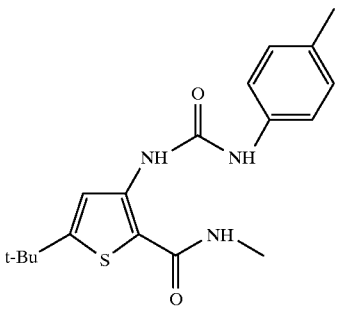

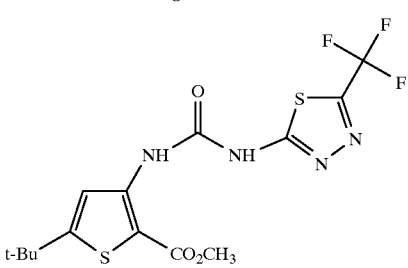

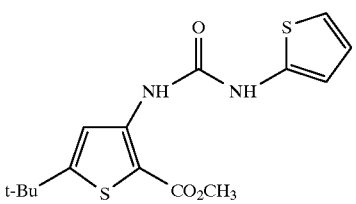

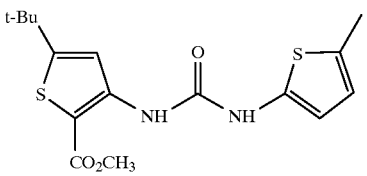

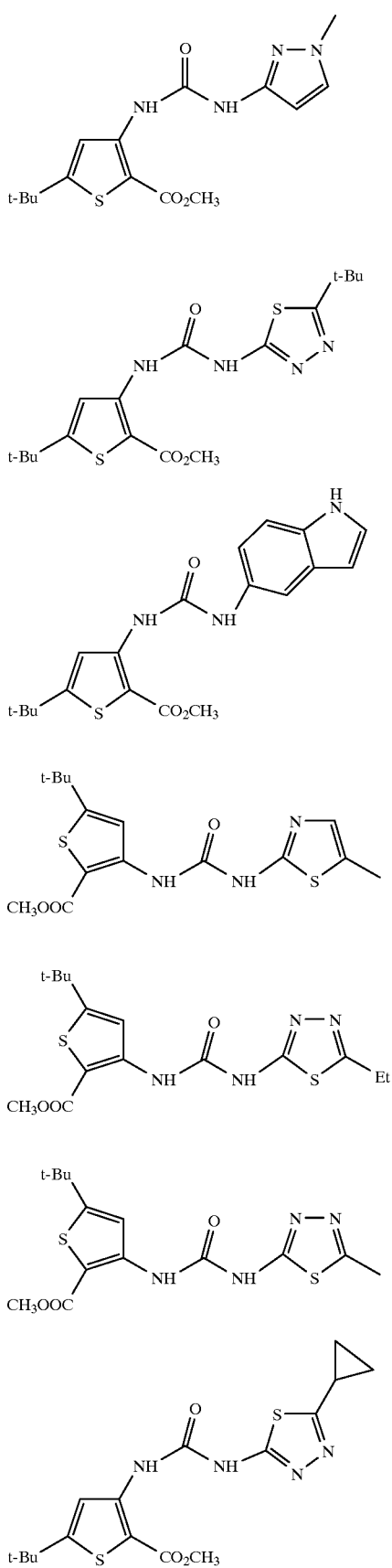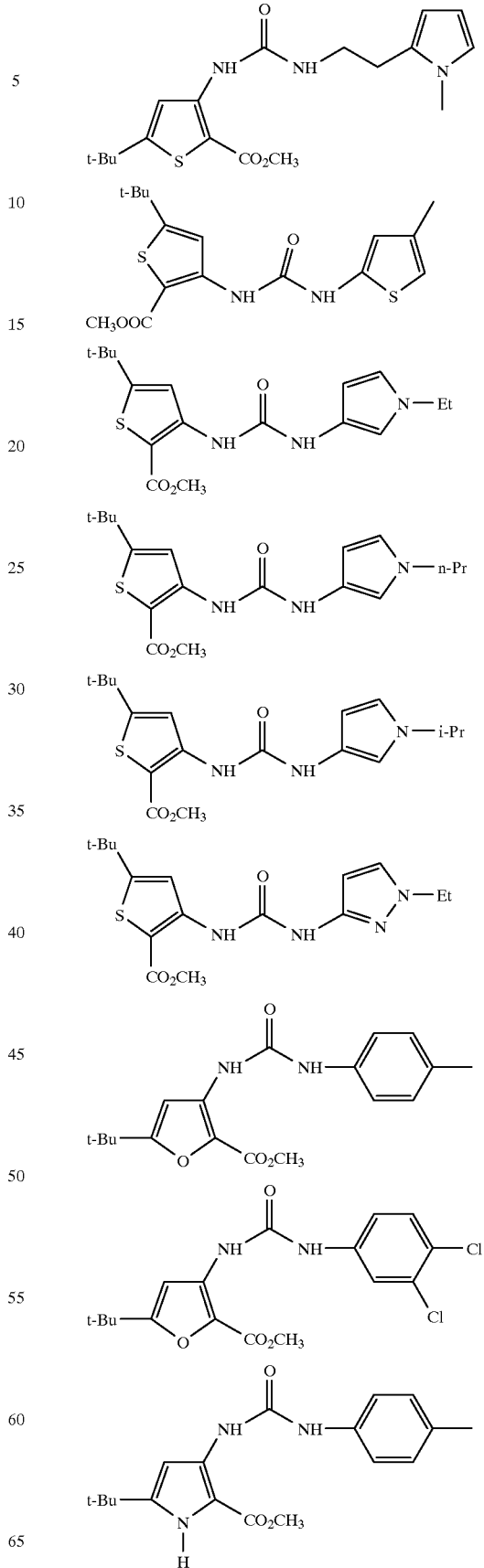

-continued
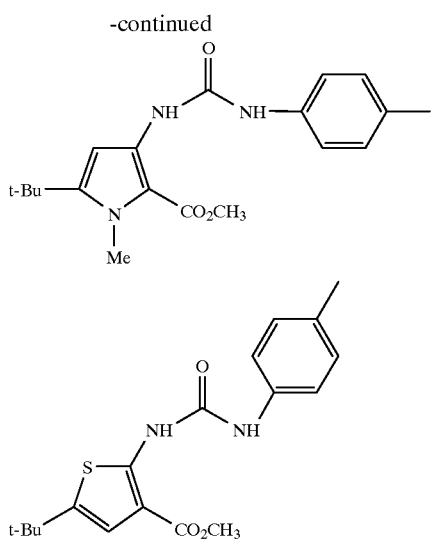
-continued
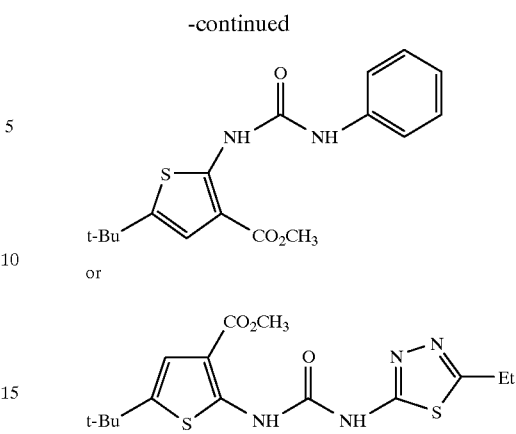
* * * * *

UNITED STATES PATENT AND TRADEMARK OFFICE
CERTIFICATE OF CORRECTION

PATENT NO.   : 6,187,799 B1                                       Page 1 of 1
DATED        : February 13, 2001
INVENTOR(S)  : Jill E. Wood et al.

It is certified that error appears in the above-identified patent and that said Letters Patent is hereby corrected as shown below:

Column 6,
Line 45, please delete the structure:

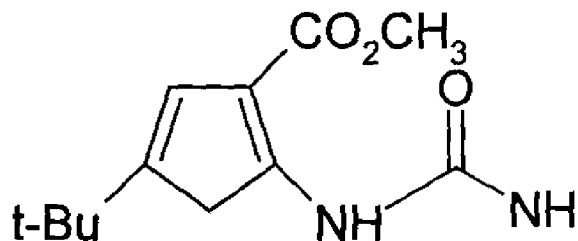

Signed and Sealed this

Thirty-first Day of December, 2002

JAMES E. ROGAN
*Director of the United States Patent and Trademark Office*